(12) United States Patent
Schlessinger et al.

(10) Patent No.: US 6,528,270 B1
(45) Date of Patent: Mar. 4, 2003

(54) METHODS FOR IDENTIFYING COMPOUNDS FOR TREATMENT OF CELL PROLIFERATIVE DISORDERS ASSOCIATED WITH ADAPTOR PROTEIN INTERACTIONS

(75) Inventors: Joseph Schlessinger, New York, NY (US); Mikhail L. Gishizky, Palo Alto, CA (US); Ann Marie Pendergast, Durham, NC (US)

(73) Assignees: Sugen, Inc., South San Francisco, CA (US); Duke University, Durham, NC (US); New York University, New York, NY (US)

( * ) Notice: Subject to any disclaimer, the term of this patent is extended or adjusted under 35 U.S.C. 154(b) by 0 days.

(21) Appl. No.: 09/393,585

(22) Filed: Sep. 9, 1999

Related U.S. Application Data

(60) Division of application No. 08/449,648, filed on May 24, 1995, now abandoned, which is a division of application No. 08/246,441, filed on May 20, 1994, now Pat. No. 6,066,463, which is a continuation-in-part of application No. 08/127,922, filed on Sep. 28, 1993, now abandoned.

(51) Int. Cl.[7] .................. G01N 33/55; G01N 33/567; G01N 33/574; C12Q 1/00; A61K 49/00

(52) U.S. Cl. .................. 435/7.1; 435/7.2; 435/7.21; 435/7.23; 435/4; 424/9.2; 436/63; 436/64; 436/518

(58) Field of Search .................. 435/4, 5, 6, 7.2, 435/7.21, 7.23, 7.24; 436/518, 63, 64; 424/9.2, 138.1

(56) References Cited

FOREIGN PATENT DOCUMENTS

| CA | 2113494 | 7/1995 |
| WO | WO94/07913 | 4/1994 |
| WO | WO94/11392 | 5/1994 |

OTHER PUBLICATIONS

Bowtell et al., 1992, "Identification of murine homologues of the Drosophila Son of Sevenless gene: potential activators of Ras", Pro Nat Acad Sci USA 89:6511–6515.

Buday and Downward, 1993, "Epidermal growth factor regulates p21Ras through the formation of a complex receptor, Grb2 adaptor protein, an Sos nucleotide exchange factor", Cell 73:611–620.

Cantley LC et al., 1991 "Oncogenes and signal transduction", Cell. Jan 25;64(2):281–302.

Chardin P et al., 1993, "Human Sos1: a guanine nucleotide exchange factor for Ras that binds to GRB2", Science, May 28; 260(5112):1338–43.

Egan SE et al., 1993, "Association of Sos Ras exchange protein with Grb2 is implicated in tyrosine kinase signal transduction and transformation", Nature. May 6; 363(6424):45–51.

Fialkow et al., 1977, "Chronic myelocytic leukemia: clonal origin in a stem cell common to the granulocyte, erythrocyte, platelet and monocyte/macrophage", Am J Med 63: 125–130.

(List continued on next page.)

Primary Examiner—Anthony C. Caputa
Assistant Examiner—Jennifer Hunt
(74) Attorney, Agent, or Firm—Foley & Lardner

(57) ABSTRACT

The present invention relates to compositions and methods for the prevention and treatment of cell proliferative disorders wherein a protein tyrosine kinase or protein tyrosine phosphatase capable of complexing with a member of the SH2- and/or SH3-containing family of adaptor proteins is involved. This invention is based, in part, on the surprising discovery that the adaptor protein, GRB-2, binds the intracellular BCR-ABL tyrosine kinase product in vivo and is necessary for the activation of the oncogenic potential of the BCR/ABL product. The present invention further relates to protein tyrosine kinase/adaptor protein complexes and the uses of these complexes for the identification of agents capable of decreasing or inhibiting the interaction between the members of such complexes.

8 Claims, 20 Drawing Sheets

OTHER PUBLICATIONS

Figure 1:
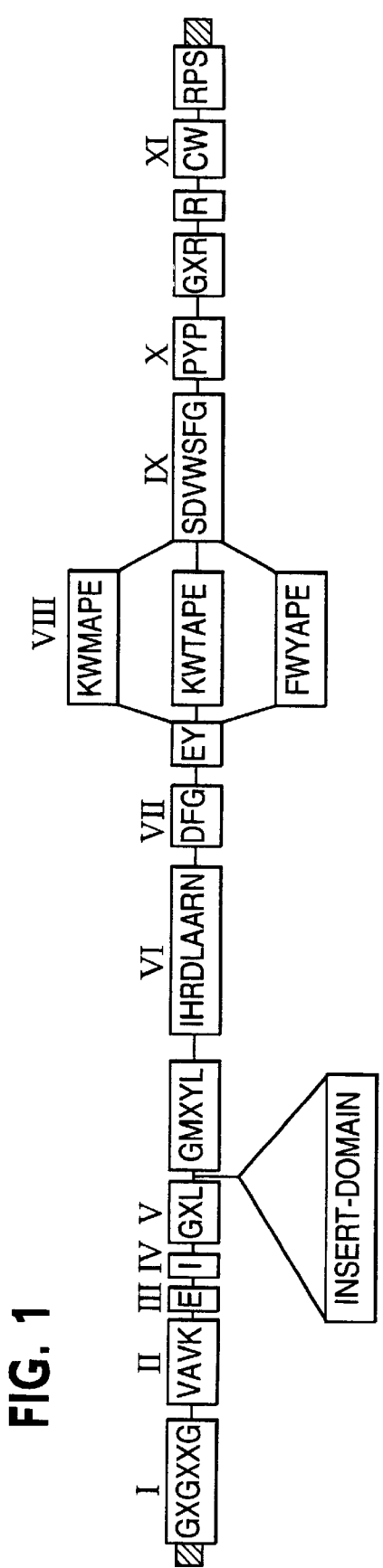

Fischer et al., 1991, "Protein tyrosine phosphatases: a diverse family of intracellular and transmembrane enzymes", Science 253:401–406.

Freidinger RM., 1989, "Non–peptide ligands for peptide receptors", Trends Pharmacol Sci. Jul; 10(7):270–4.

Gale et al., 1993, "Grb2 mediates the EGF–dependent activation of guanine nucleotide exchange of Ras", Nature 363:88–92.

Hardie, 1990, "Roles of protein kinases and phosphatases in signal transduction", Symp Soc Exp Biol 44:241–255.

Hunter, 1991, "Cooperation between oncogenes", Cell 64:249–270.

Koch et al., 1991, "SH2 and SH3 domains: elements that control interactions of cytoplasmic signaling proteins", Science 252:668–674.

Konopka et al., 1984, "an alteration of the human c–abl protein in K562 leukemia cells unmasks associated tyrosine kinase activity", Cell 37:1035–1042.

Kruh et al., 1986, "A novel human gene closely related to the abl proto–oncogene", Science 234:1545–1548.

Kurzrock et al., 1988, "The molecular genetics of Philadelphia chromosome–positive leukemias", N Engl J Med 319:990–998.

Li et al., 1993, "Guanine–nucleotide–releasing factor hSos1 binds to Grb2 and links receptor tyrosine kinases to Ras signalling", Nature 363:85–87.

Liebow C et al., 1989, "Somatostatin analogues inhibit growth of pancreatic cancer by stimulating tyrosine phosphatase", Proc Natl Acad Sci U S A. Mar; 86(6):2003–7.

Liu et al., 1993, "BCR–ABL tyrosine kinase is autophosphorylated or transphosphorylates P160 BCR on tyrosine predominantly within the first BCR exon", Oncogene 8:101–109.

Lowenstein et al., 1992, "The SH2 and SH3 domain–containing protein GRB2 links receptor tyrosine kinases to ras signaling", Cell 70:431–442.

Lowy and Willumsen, 1993, "Function and regulation of Ras", Ann Rev Biochem 62:851–891.

Mayer et al., 1988, "A novel viral oncogene with structural similarity to phospholipase C", Nature 332:272–275.

McWhirter and Wang, 1991, "Activation of tyrosine kinase and the microfilament–binding functions of c–abl by bcr sequences in bcr/abl fusion proteins", Mol and Cell Biol 11:1553–1565.

Muller et al., 1992, "A limited set of SH2 domains binds BCR through a high affinity phosphotyrosine–independent interaction", Mol and Cell Biol 12:5087–5093.

Muller et al., 1991, "BCR first exon sequences specifically activate the BCR/ABL tyrosine kinase oncogene of Philadelphia chromosome–positive human leukemias", Mol and Cell Biol. 11:1785–1792.

Nurse, 1990, "Universal control mechanism regulating onset of M–phase", Nature 344:503–508.

Olivier et al., 1993, "A Drosophila SH2–SH3 adaptor protein implicated in coupling the Sevenless tyrosine kinase to an activator of Ras guanine nucleotide exchange, Sos", Cell 73:179–191.

Pawson and Schlessinger, 1993, "SH2 and SH3 domains", Curr Biol 3:434–442.

Pelicci G et al., 1992, "A novel transforming protein (SHC) with an SH2 domain is implicated in mitogenic signal transduction", Cell. Jul. 10; 70(1):93–104.

Pendergast AM et al., 1993, "BCR–ABL–induced oncogenesis is mediated by direct interaction with the SH2 domain of the GRB–2 adaptor protein", Cell Oct. 8; 75(1):175–85.

Pendergast et al., 1991, "BCR sequences essential for transformation by the BCR–ABL oncogene bind to the ABL SH2 regulatory domain in a non–phosphotyrosine–dependent manner", Cell 66:161–171.

Pendergast et al., 1991, "Evidence for regulation of the human ABL tyrosine kinase by a cellular inhibitor", Proc Nat Acad Sci USA 88:5927–5931.

Posada and Cooper, 1992, "Molecular signal integration. Interplay between serine, threonine, and tyrosine phosphorylation", Mol Biol Cell 3:583–592.

Rosenberg and Witte, 1988, "The viral and cellular forms of the Abelson (abl) oncogene", Advances in Virus Research 35:39–81.

Rozakis–Adcock M et al., 1992, Association of the Shc and Grb2/Sem5 SH2–containing proteins is implicated in activation of the Ras pathway by tyrosine kinases, Nature. Dec. 17;360(6405):689–92.

Rozakis–Adcock M et al., 1993, "The SH2 and SH3 domains of mammalian Grb2 couple the EGF receptor to the Ras activator mSos1", Nature. May 6; 363(6424):83–5.

Sadowski et al., 1986, "A noncatalytic domain conserved among cytoplasmic protein–tyrosine kinases modifies the kinase function and transforming activity of Fujinami sarcoma virus P130gag–fps", Mol and Cell Biol 6:4396–4408.

Sarzani et al., 1992, "A novel endothelial tyrosine kinase cDNA homologous to platelet–derived growth factor receptor cDNA", Biochem Biophys Res Commun (United States) 186(2):706–714.

Schlessinger and Ullrich, 1992, "Growth factor signaling by receptor tyrosine kinases", Neuron 9:383–391.

Schlessinger, 1993, "How receptor tyrosine kinases activate Ras", TIBS 18:273–275.

Shepard HM et al., 1991,"Monoclonal antibody therapy of human cancer: taking the HER2 protooncogene to the clinic", J Clin Immunol. May/ 11(3):117–27.

Shtivelman et al., 1986, "Alternative splicing of RNAs transcribed from the human abl gene and from the bcr–abl fused gene", Cell 47:277–284.

Simon et al., 1993, "An SH3–SH2–SH3 protein is required for $p21^{Ras1}$ activation and binds to Sevenless and Sos proteins in vitro", Cell 73:169–177.

Skolnik EY et al., 1993, "The SH2/SH3 domain–containing protein GRB2 interacts with tyrosine–phosphorylated IRS1 and Shc: implications for insulin control of ras signalling", EMBO J. May; 12(5):1929–36.

Skorski et al., 1993, "Highly efficient elimination of Philadelphia leukemia cells by exposure to bcr/abl antisense oligodeoxynucleotides combined with mafosfaimde", J Clin Invest 92:194–202.

Snyder et al., 1993, "Ribozyme–mediated inhibition of bcr/abl gene expression in a Philadelphia chromosome–positive cell line", Blood 82:600–605.

Timmons and Witte, 1989, "Structural characterization of the BCR gene product", Oncogene 4:559–567.

Ullrich and Schlessinger, 1990, "Signal transduction by receptors with tyrosine kinase activity", Cell 61:203–212.

Wilks, 1990, "Structure and function of the protein tyrosine kinases", Progress in Growth Factor Research 2:97–111.

Zhang et al., 1992, "Activation of phospholipase D by platelet–derived growth factor (PDGF) in rat C6 glioma cells: possible role in mitogenic signal transduction", Neurol Res (England) 14(5):397–401.

Pawson and Gish, 1992, "SH2 and SH3 domains:from structure to function", Cell 71:359–362.*

* cited by examiner

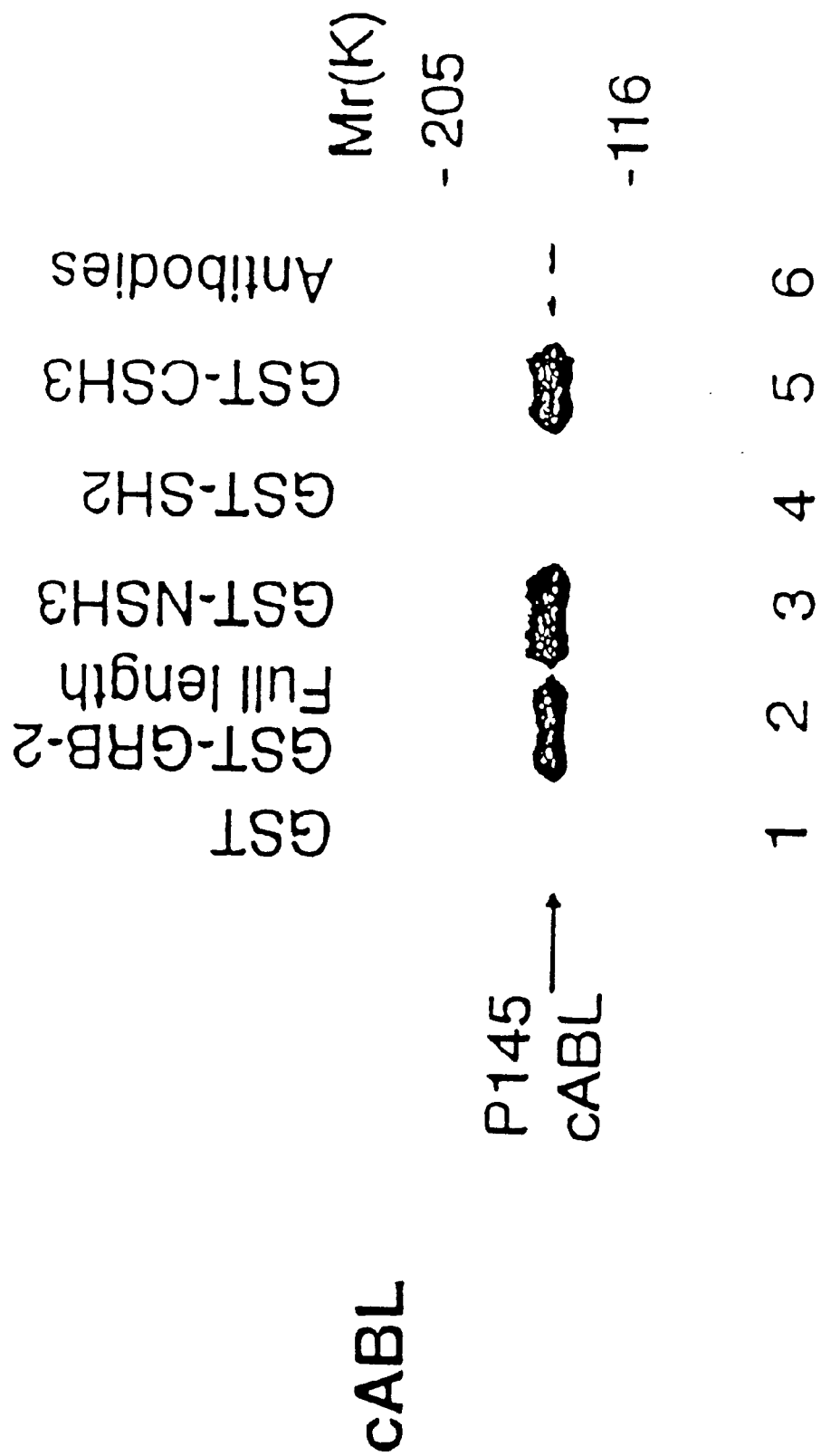

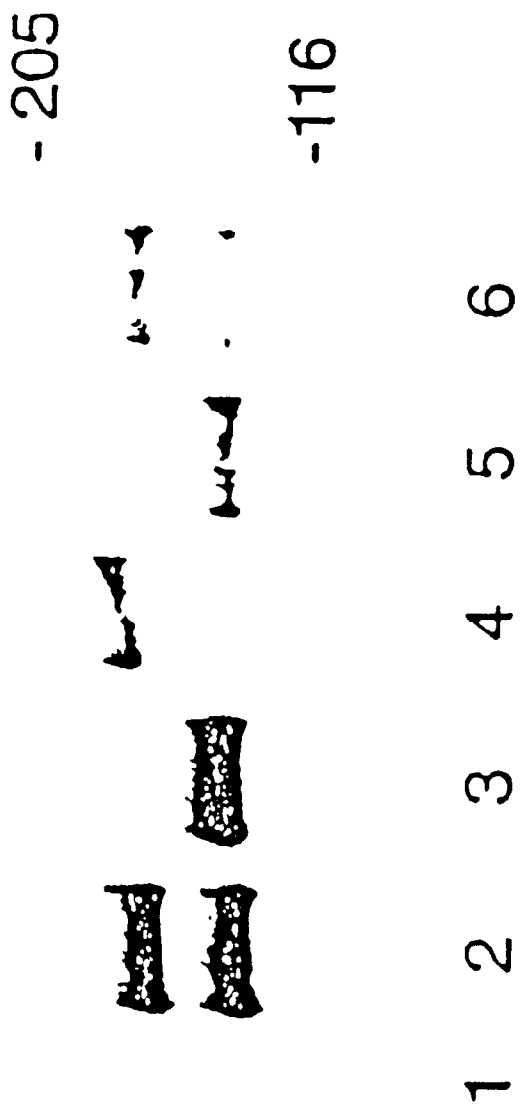

NRS  αBCR  αGRB-2    Mr(K)

- 205

BCR →                        -116
Δ(872-1271)

1    2    3

FIG. 10

| Retroviral[a] Constructs | P185 Variants BCR / ABL | Rat1[b] #colonies/10⁵cells | | Bone Marrow[c] Transformed/total |
|---|---|---|---|---|
| | | Acutely Infected[c] | G418 Selected[d] | |
| P185 wild type | | 37 | 690 | 11/12 |
| P185 (Y177F) | | 0 | 40 | 0/14 |
| P185 (Δ176-426) | | 0 | 10 | 0/9 |
| vector | | 0 | 0 | 0/7 |

CO-EXPRESSION OF P210 BCR/ABL WITH GRB2 WILD TYPE AND MUTANT FORMS IN RAT 1 FIBROBLASTS

STIMULATION OF TRANSCRIPTIONAL ACTIVATION BY BCR-ABL THROUGH RAS IS PARTIALLY BLOCKED BY GRB2 MUTANTS

1: RAT1
2: RAT1/p210/pCGN Vector
3: RAT1/p210/pCGN Grb2 ΔN'
4: RAT1/p210/PCGN Grb2 ΔC'

Normalized RAT1 to 1

Values are mean of duplicate ± range.

METHODS FOR IDENTIFYING COMPOUNDS FOR TREATMENT OF CELL PROLIFERATIVE DISORDERS ASSOCIATED WITH ADAPTOR PROTEIN INTERACTIONS

This is a division of application Ser. No. 08/449,648, filed May 24, 1995 now abandoned which is a division of application Ser. No. 08/246,441 filed May 20, 1994 now U.S. Pat. No. 6,066,463, which is a continuation-in-part of Ser. No. 08/127,922 filed Sep. 28, 1993, now abandoned, each of which is incorporated herein in their entirety.

1. INTRODUCTION

The present invention relates to compositions and methods for the prevention and treatment of cell proliferative disorders wherein a protein tyrosine kinase or protein tyrosine phosphatase capable of complexing with a member of the SH2- and/or SH3-containing family of adaptor proteins is involved. This invention is based, in part, on the surprising discovery that the adaptor protein, GRB-2, binds the intracellular BCR-ABL tyrosine kinase product in vivo and is necessary for the activation of the oncogenic potential of the BCR-ABL product and that disruption of the signaling capability of GRB-2 can reverse the transformed phenotype of cells and reduce tumor growth in animals. The present invention further relates to protein tyrosine kinase/adaptor protein complexes and the uses of these complexes for the identification of agents capable of disrupting the interaction between the members of such complexes.

2. BACKGROUND

2.1. Protein Phosphorylation and Signal Transduction

Cells rely, to a great extent, on extracellular molecules as a means by which to receive stimuli from their immediate environment. These extracellular signals are essential for the correct-regulation of such diverse cellular processes as differentiation, contractility, secretion, cell division, contact inhibition, and metabolism. The extracellular molecules, which can include, for example, hormones, growth factors, lymphokines, or neurotransmitters, act as ligands that bind specific cell surface receptors. The binding of these ligands to their receptors triggers a cascade of reactions that brings about both the amplification of the original stimulus and the coordinate regulation of the separate cellular processes mentioned above. In addition to normal cellular processes, receptors and their extracellular ligands may be involved in abnormal or potentially deleterious processes such as virus-receptor interaction, inflammation, and cellular transformation to a cancerous state.

A central feature of this process, referred to as signal transduction (for recent reviews, see Posada et al., 1992, Mol. Biol. Cell 3:583–592; Hardie, D. G., 1990, Symp. Soc. Exp. Biol. 44:241–255), is the reversible phosphorylation of certain proteins.

The phosphorylation or dephosphorylation of amino acid residues triggers conformational changes in regulated proteins that alter their biological properties. Proteins are phosphorylated by protein kinases and are dephosphorylated by protein phosphatases. Protein kinases and phosphatases are classified according to the amino acid residues they act on, with one class being serine-threonine kinases and phosphatases (reviewed in Scott et al., 1992, 2:289–295), which act on serine and threonine residues, and the other class being the tyrosine kinases and phosphatases (reviewed in Fischer et al., 1991, Science 253:401–406; Schlessinger et al., 1992, Neuron 9:383–391; Ullrich et al., 1990, Cell 61:203–212), which act on tyrosine residues. Phosphorylation is a dynamic process involving competing phosphorylation and dephosphorylation reactions, and the level of phosphorylation at any given instant reflects the relative activities, at that instant, of the protein kinases and phosphatases that catalyze these reactions.

While the majority of protein phosphorylation occurs at serine and threonine amino acid residues, phosphorylation at tyrosine residues also occurs, and has begun to attract a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Cantley et al., 1991, Cell 64:281–302; Hunter T., 1991, Cell 64:249–270; Nurse, 1990, Nature 344:503–508; Schlessinger et al., 1992, Neuron 9:383–391; Ullrich et al., 1990, Cell 61:203–212). Subversion of normal growth control pathways leading to oncogenesis has been shown to be caused by activation or overexpression of protein tyrosine kinases which constitute a large group of dominant oncogenic proteins (reviewed in Hunter, T., 1991, Cell 64:249–270).

2.2. Protein Tyrosine Kinases

Protein tyrosine kinases comprise a large family of proteins, including many growth factor receptors and potential oncogenes, which share ancestry with, but nonetheless differ from, serine/threonine-specific protein kinases (Hanks et al., 1988, Science 241:42–52). The protein kinases may further be defined as being receptors or non-receptors.

Receptor-type protein tyrosine kinases, which have a transmembrane topology have been studied extensively. The binding of a specific ligand to the extracellular domain of a receptor protein tyrosine kinase is thought to induce receptor dimerization and phosphorylation of their own tyrosine residues. Individual phosphotyrosine residues of the cytoplasmic domains of receptors may serve as specific binding sites that interact with a host of cytoplasmic signalling molecules, thereby activating various signal transduction pathways (Ullrich et al., 1990, Cell 61:203–212).

The intracellular, cytoplasmic, non-receptor protein tyrosine kinases may be broadly defined as those protein tyrosine kinases which do not contain a hydrophobic, transmembrane domain. Within this broad classification, one can divide the known cytoplasmic protein tyrosine kinases into four distinct morphotypes: the SRC family (Martinez et al., 1987, Science 237:411–414; Sukegawa et al., 1987, Mol. Cell. Biol. 7:41–47; Yamanishi et al., 1987, 7:237–243; Marth et al., 1985, Cell 43:393–404; Dymecki et al., 1990, Science 247:332–336), the FES family (Ruebroek et al., 1985, EMBO J. 4:2897–2903; Hao et al., 1989, Mol. Cell. Biol. 9:1587–1593), the ABL family (Shtivelman et al., 1986, Cell 47:277–284; Kruh et al., 1986, Science 234:1545–1548), and the JAK family. While distinct in their overall molecular structure, each of the members of these morphotypic families of cytoplasmic protein tyrosine kinases share non-catalytic domains in addition to sharing their catalytic kinase domains. Such non-catalytic domains are the SH2 (SRC homology domain 2; Sadowski et al., Mol. Cell. Biol. 6: 4396–4408; Koch et al., 1991, Science 252:668–674) domains and SH3 domains (Mayer et al., 1988, Nature 332:269–272). Non-catalytic domains are thought to be important in the regulation of protein-protein interactions during signal transduction (Pawson et al., 1992, Cell 71:359–362).

While the metabolic roles of cytoplasmic protein tyrosine kinases are less well understood than that of the receptor-type protein tyrosine kinases, significant progress has been made in elucidating some of the processes in which this class of molecules is involved. For example, lck and fyn, members of the src family, have been shown to interact with CD4/CD8 and the T cell receptor complex, and are thus implicated in T cell activation, (Veillette et al., 1992, *TIG* 8:61–66). Certain cytoplasmic protein tyrosine kinases have been linked to certain phases of the cell cycle (Morgan et al., 1989, *Cell* 57:775–786; Kipreos et al., 1990, *Science* 248: 217–220; Weaver et al., 1991, *Mol. Cell. Biol.* 11:4415–4422). Cytoplasmic protein tyrosine kinases have been implicated in neuronal development (Maness, P., 1992, *Dev. Neurosci.* 14:257–270). Deregulation of kinase activity through mutation or overexpression is a well-established mechanism underlying cell transformation (Hunter et al., 1985, supra; Ullrich et al., supra).

2.3. G-Proteins and Signal Transduction

Guanine-nucleotide-binding proteins, (G-proteins; Simon et al., 1991, *Science* 252:802–808; Kaziro et al., 1991, *Ann. Rev. Biochem.* 60:349–400) such as Ras (for review, see Lowy et al., 1993, *Ann Rev. Biochem.* 62:851–891), play an essential role in the transmission of mitogenic signals from receptor tyrosine kinases. Taking Ras as an example, the activation of receptor tyrosine kinases by ligand binding results in the accumulation of the active GTP bound form of the Ras molecule (Gibbs et al., 1990, *J. Biol. Chem.* 265:20437–2044; Satoh et al., 1990, *Proc. Natl. Acad. Sci. USA* 87:5993–5997; Li et al., 1992, *Science* 256:1456–1459; Buday et al., 1993, *Mol. Cell. Biol.* 13:1903–1910; Medema et al., 1993, *Mol. Cell. Biol.* 13:155–162). Ras activation is also required for transformation by viral oncogenic tyrosine kinases (Smith et al., 1986, *Nature* 320:540–43).

Ras activity is regulated by the opposing actions of the GTPase-activating proteins (GAPs) and guanine nucleotide exchange factors, with GAPs stimulating the slow intrinsic rate of GTP hydrolysis on Ras and exchange factors stimulating the basal rate of exchange of GDP for GTP on Ras. Thus, GAPS act as negative regulators of Ras function, while exchange factors act as Ras activators.

Recently, a direct link between activated receptor tyrosine kinases and Ras was established with the finding that the mammalian GRB-2 protein, a 26 kilodalton protein comprised of a single SH2 and two SH3 domains (Lowenstein et al., 1992, *Cell* 70:431–442), directly couples receptor tyrosine kinases to the Ras exchange factor Sos in mammals and Drosophila (Buday et al., 1993, *Cell* 73:611–620; Egan et al., 1993, *Nature* 363:45–51; Li et al., 1993, *Nature* 363:85–87; Gale et al., 1993, *Nature* 363:88–92; Rozakis-Adcock et al., 1993, *Nature* 363:83–85; Chardin et al., 1993, *Science* 260:1338–1343; Oliver et al., *Cell* 73:179–191; Simon et al., 1993, *Cell* 73:169–177). The GRB-2 SH2 domain binds to specific tyrosine phosphorylated sequences in receptor tyrosine kinases while the GRB-2 SH3 domains bind to proline-rich sequences present in the Sos exchange factor. Binding of GRB-2 to the receptor kinases, therefore, allows for the recruitment of Sos to the plasma membrane, where Ras is located (Schlessinger, J., 1993, *TIBS* 8:273–275).

2.4. BCR-ABL in the Development of Leukemias

Activation of the oncogenic potential of normal cellular proteins such as protein tyrosine kinases may occur by alteration of the proteins' corresponding enzymatic activities, their inappropriate binding to other cellular components, such as those mentioned above in Section 2.3, or both.

For example, the BCR-ABL protein tyrosine kinase oncoprotein may transform cells via changes in enzyme activity and/or altering of noncovalent protein-protein interactions. The gene encoding the BCR-ABL oncoprotein is a chimeric oncogene generated by the translocation of sequences from the cABL protein tyrosine kinase on chromosome 9 into BCR sequences on chromosome 22 (reviewed in Kurzock et al., 1988, *N. Engl. J. Med.* 319:990–998, and Rosenberg et al., 1988, *Adv. in Virus Res.* 35:39–81). The BCR-ABL oncogene has been implicated in the pathenogenesis of Philadelphia chromosome (Ph[1]) positive human leukemias. Namely, the Ph[1] chromosome is found in at least 90 to 95 percent of cases of chronic myelogenous leukemia (CML), which is a clonal cancer arising from the neoplastic transformation of hematopoietic stem cells (Fialkow et al., 1977, *Am. J. Med.* 63:125–130), and is also observed in approximately 20 percent of adults with acute lymphocytic leukemia (ALL), 5 percent of children with ALL, and 2 percent of adults with acute myelogenous leukemia (AML) (Whang-Peng et al., 1970, *Blood* 36:448–457; Look, A. T., 1985, *Semin. Oncol.* 12:92–104). The BCR-ABL gene produces two alternative chimeric proteins, P210 BCR-ABL, and P185 BCR-ABL, which are characteristic of CML and ALL, respectively. Further, it has recently been directly demonstrated that the BCR-ABL gene product is the causative agent in CML (Skorski et al., 1993, *J. Clin Invest.* 92:194–202; Snyder et al., 1993, *Blood* 82:600–605).

Clinically, CML is characterized by a biphasic course. The disease begins with a chronic phase marked by a greatly increased pool of uncommitted myeloid progenitor cells. Because terminal differentiation is maintained, this results in greatly increased pools of circulating mature granulocytes. After a period of several weeks to many years, a state of accelerated myeloproliferation develops wherein the myeloid cells progressively lose their capacity for terminal differentiation. During this time, thrombocytosis, basophilia, and clonal cytogenetic abnormalities often appear. These abnormalities signal the terminal, blast-crisis stage, during which immature blast cells rapidly proliferate and the patient inevitably dies.

It has previously been shown that the BCR-ABL proteins exhibit heightened tyrosine kinase and transforming capabilities compared to the normal c-ABL protein (Konopka et al., 1984, *Cell* 37:1035–1042). BCR first exon sequences specifically activate the tyrosine kinase and transforming potential of BCR-ABL (Muller et al., 1991, *Mol. Cell. Biol.* 11:1785–1792; McWhirter et al., 1991, *Mol. Cell. Biol.* 11:1553–1565). The BCR first exon is capable of binding to the ABL SH2 domain in a phosphotyrosine-independent manner (Pendergast et al., 1991, *Cell* 66:161–171), and deletion of BCR sequences essential for ABL SH2-binding render BCR-ABL nontransforming (Pendergast et al., 1991, *Cell* 66:161–171). In addition, it has been demonstrated that BCR binds, in vitro, to some other SH2 domains encoded by other proteins (Muller et al., 1992, *Mol. Cell. Biol.* 12:5087–5093). While one may infer from these results that some aspect of SH2 domain-binding to BCR is involved in the oncogenicity of the BCR-ABL oncoprotein, the mechanism by which such BCR-ABL oncogenesis occurs is still obscure. For example, given the myriad of SH2-containing proteins which are known to exist, the identification of a BCR-ABL effector(s) will necessitate much further study.

3. SUMMARY OF THE INVENTION

The present invention relates to compositions and methods for the prevention and treatment of cell proliferative disorders wherein a protein tyrosine kinase or a protein tyrosine phosphatase capable of complexing with a member of the SH2- and/or SH3-containing family of adaptor proteins is involved. The present invention further relates to protein tyrosine kinase/adaptor protein complexes, protein tyrosine phosphatase/adaptor protein complexes, and the uses of these complexes for the identification of agents capable of disrupting the interaction between the components of such complexes.

"Protein tyrosine kinase" will, herein, be abbreviated "PTK", and "protein tyrosine phosphatase" will, herein be abbreviated "PTP". It is to be understood that "PTK" may refer to either a transmembrane, receptor-type protein tyrosine kinase or a cytoplasmic protein tyrosine kinase, unless otherwise indicated, and, likewise, "PTP" may refer to either a transmembrane, receptor-type protein tyrosine phosphatase or a cytoplasmic protein tyrosine phosphatase, unless otherwise indicated.

This invention is based, in part, on the surprising discovery that the adaptor protein, GRB-2, binds the intracellular BCR-ABL PTK product in vivo and is necessary for the activation of the oncogenic potential of the BCR-ABL product. The inventors are the first to demonstrate the physiological relevance of the interactions between the members of a signal transduction pathway, in part by showing that disruption of this signal transduction can result in the reversal of the transformed phenotype of cells and inhibit tumor growth in animals. The data representing this discovery is presented in the Working Examples in Sections 6 through 12, below. The invention, therefore, represents the first instance whereby the SH2- and/or SH3-containing adaptor family of proteins, especially the GRB-2 member of the GRB subfamily of proteins, are implicated in the development and maintenance of cell proliferation/activation— herein demonstrated for the abnormal cellular proliferation involved in oncogenesis, the transformation process, and the development of human cancer. Still further, with respect to BCR-ABL transformation, the present invention discloses the first effector (i.e., GRB-2) for the BCR-ABL product.

3.1. Abbreviations

The following table lists the single-letter and triple-letter abbreviations for amino acids that are in common use among protein chemists and that are used herein.

| Amino Acid | One Letter Code | Three Letter Code |
|---|---|---|
| Alanine | A | Ala |
| Arginine | R | Arg |
| Asparagine | N | Asn |
| Aspartic Acid | D | Asp |
| Cysteine | C | Cys |
| Glutamic Acid | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methioine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Not Specified | X | |

4. DESCRIPTION OF THE FIGURES

FIG. 1. Conserved motifs of the catalytic domains of PTKs (SEQ ID NOS: 11–17). (From Wilks, A. F., 1990, *Progress in Growth Fact. Res.* 2:97–111)

Figure 2:
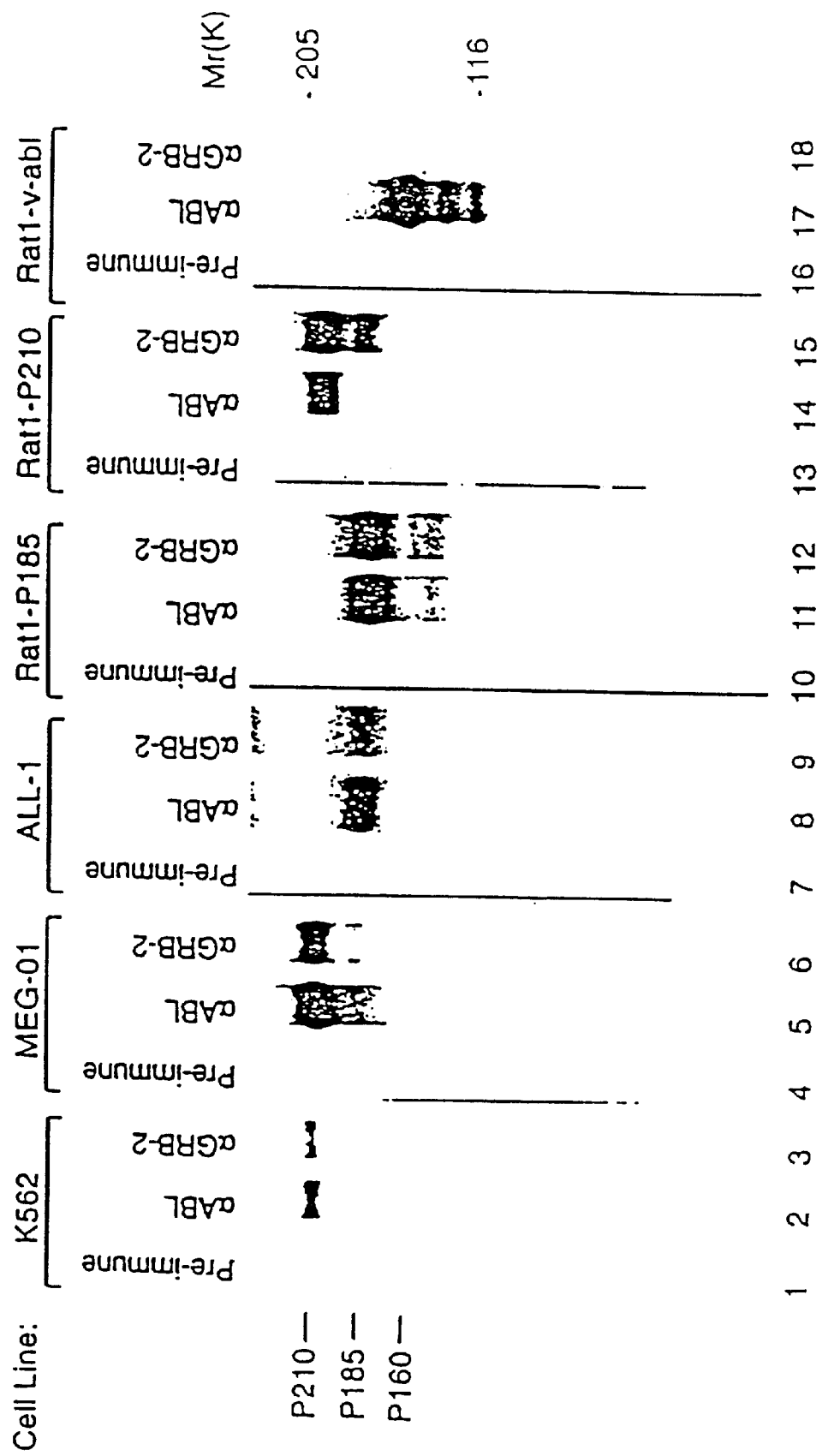

FIG. 2. BCR-ABL binds to the GRB-2 adaptor protein in living cells. K562, MEG-01 and ALL-1 Ph[1] hematopoietic cells and Rat1 fibroblasts expressing P185 BCR-ABL, P210 BCR-ABL, and P160 v-abl proteins were lysed and the lysates incubated with pre-immune sera (lanes 1, 4, 7, 10, 13, 16), anti-ABL pEX4 antibodies (lanes 2, 5, 6, 11, 14, 17) and anti-GRB2 antibodies (lanes 3, 6, 9, 12, 15, 18). The immunoprecipitates were collected on protein A-Sepharose beads and subjected to in vitro phosphorylation in the presence of [$\gamma^{32}$-P] ATP and $MnCl_2$. The reactions were terminated after 30 min. at 30° C., washed and analyzed by SDS 8% polyacrylamide gel electrophoresis. The $^{32}$P-labeled proteins were detected by autoradiography.

Figure 3:
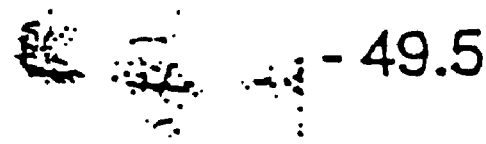
Figure 3:
Figure 3:

FIG. 3. GRB-2 co-immunoprecipitates with BCR-ABL. MEG-01 cells were lysed and the lysate incubated with pre-immune sera (lane 1), anti-ABL pEX4 antibodies (lane 2) and anti-GRB-2 antibodies (lane 3). The immunoprecipitated proteins were separated by SDS 12.5% polyacrylamide gel electrophoresis, transferred to nitrocellulose and immunoblotted with anti-GRB-2 antibodies. Bound antibodies were visualized with [$^{125}$I] protein A.

Figure 4:
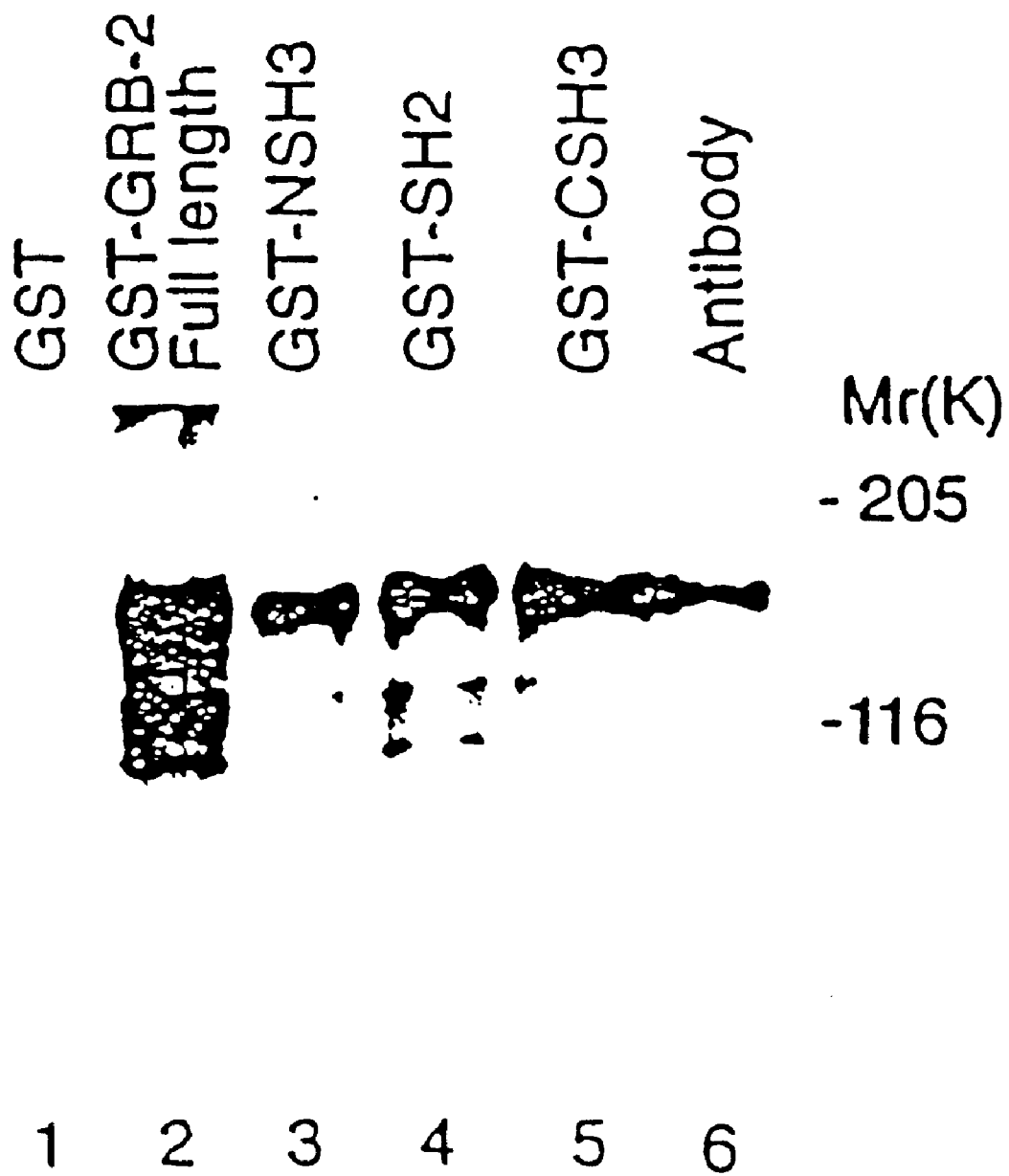

FIG. 4. BCR-ABL binds to GRB-2 in vitro. [$^{35}$S] methionine-labeled proteins from lysates of Sf9 insect cells infected with P185 BCR-ABL recombinant baculovirus were incubated with equal amounts of immobilized GST alone (lane 1), GST-GRB-2 full length (lane 2), GST-aminoterminal (N) GRB-2 SH3 domain (lane 3), GST-GRB-2 SH2 domain (lane 4), GST-carboxy-terminal (C) GRB-2 SH3 domain (lane 5) and anti-ABL antibodies bound to protein A-Sepharose beads (lane 6). After incubation for 90 min. at 4° C., the beads were washed four times with incubation buffer and twice with RIPA buffer to remove unbound material. Bound proteins were analyzed by SDS 7% polyacrylamide gel electrophoresis and detected by fluorography.

FIG. 5A. SH2 domain-mediated binding of GRB-2 to BCR-ABL requires tyrosine phosphorylation of BCR sequences. Sf9 insect cells were singly infected with cABL recombinant baculoviruses. Three days post-infection, the cells were labeled with [$^{35}$S] methionine. The labeled cells were lysed and the lysate proteins incubated with GST alone (lanes 1), GST-GRB-2 full length (lanes 2), GST-GRB-2 N SH3 (lanes 3), GST-GRB-2 SH2 (lanes 4), GST-GRB-2 C SH3 (lanes 5) and the corresponding anti-ABL (lane 6) antibodies in the presence of protein A-Sepharose beads. After incubation for 90 min. at 4° C., the beads were washed four times with incubation buffer and twice with RIPA buffer. Bound proteins were analyzed by SDS 10% polyacrylamide gel electrophoresis and detected by fluorography.

Figure 5B:

FIG. 5B. SH2 domain-mediated binding of GRB-2 to BCR-ABL requires tyrosine phosphorylation of BCR sequences. Sf9 insect cells were singly infected with CBCR recombinant baculoviruses. Three days post-infection, the cells were labeled with [$^{35}$S] methionine. The labeled cells were lysed and the lysate proteins incubated with GST alone (lanes 1), GST-GRB-2 full length (lanes 2), GST-GRB-2 N SH3 (lanes 3), GST-GRB-2 SH2 (lanes 4), GST-GRB-2 C SH3 (lanes 5) and anti-BCR (lane 6) antibodies in the presence of protein A-Sepharose beads. After incubation for 90 min. at 4° C., the beads were washed four times with incubation buffer and twice with RIPA buffer. Bound proteins were analyzed by SDS 10% polyacrylamide gel electrophoresis and detected by fluorography.

FIG. 5C. SH2 domain-mediated binding of GRB-2 to BCR-ABL requires tyrosine phosphorylation of BCR sequences. Sf9 insect cells were coinfected with cABL and cBCR recombinant baculoviruses. Three days post-infection, the cells were labeled with [$^{35}$S] methionine. The labeled cells were lysed and the lysate proteins incubated with GST alone (lanes 1), GST-GRB-2 full length (lanes 2), GST-GRB-2 N SH3 (lanes 3), GST-GRB-2 SH2 (lanes 4), GST-GRB-2 C SH3 (lanes 5) and the corresponding anti-ABL and anti-BCR (lane 6) antibodies in the presence of protein A-Sepharose beads. After incubation for 90 min. at 4° C., the beads were washed four times with incubation buffer and twice with RIPA buffer. Bound proteins were analyzed by SDS 10% polyacrylamide gel electrophoresis and detected by fluorography.

Figure 6A:
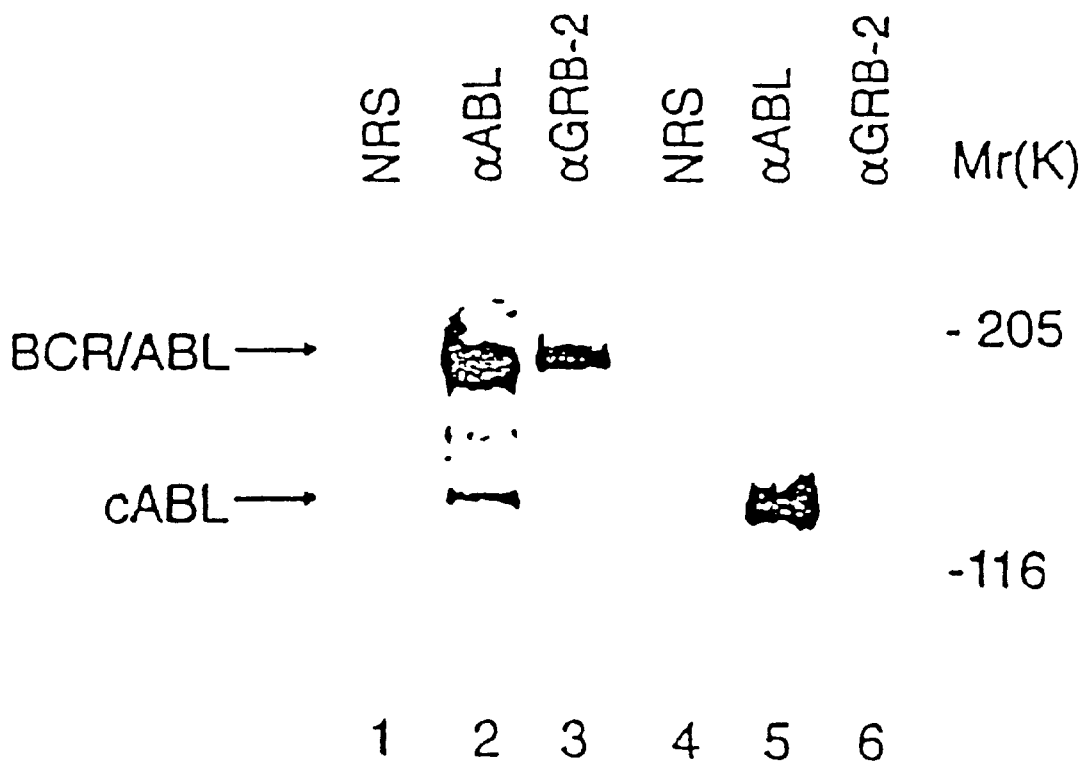

FIG. 6A. GRB-2 forms a complex with the chimeric BCR-ABL tyrosine kinase but not with cABL and CBCR sequences in vivo. COS cells were transfected with P185 wild type (lane 1–3) and cABL (lanes 4–6) cDNAs cloned into the pSRα vector. Three days post-transfection, the cells were lysed and the lysates incubated for 2 hrs. at 4° C. with normal rabbit sera (NRS) (lanes 1 and 4), anti-ABL 2/3 antibodies (lanes 2 and 5) and anti-GRB-2 antibodies (lanes 3 and 6). The immunoprecipitates were collected on protein A-Sepharose beads and washed six times with incubation buffer. Bound proteins were analyzed by SDS 8% polyacrylamide gel electrophoresis, transferred to nitrocellulose filters and the filters incubated with anti-ABL mouse monoclonal antibody. Immunoreactive bands were visualized with the enhanced chemiluminescence (ECL) detection system (Amersham).

Figure 6B:

FIG. 6B. GRB-2 forms a complex with the chimeric BCR-ABL tyrosine kinase but not with cABL and cBCR sequences in vivo. COS cells were transfected with BCR (Δ872–1271) cDNA cloned into the pSRα vector. The cells were lysed three days post-infection and the lysates incubated with control sera (NRS) (lane 1), anti-BCR antibodies (lanes 2), or anti-GRB-2 antibodies (lane 3) for 2 hrs. at 4° C. The immunoprecipitates were collected with protein A-Sepharose beads, washed four times with incubation buffer and twice with 50 mM Tris-HCl, pH 7.0 and then subjected to in vitro phosphorylation in the presence of γ-$^{32}$P-ATP and MnCl$_2$. Proteins were analyzed by SDS 8% polyacrylamide gel electrophoresis and autoradiography.

Figure 7:
Figure 7:

FIG. 7. Phosphopeptide maps of wild type and (Y177F) forms of BCR-ABL. COS cells were transfected with P185 wild type and P185 (Y177F) cloned into the pSRαMSVtkneo vector. Three days post-transfection, the cells were lysed and the lysates incubated with anti-ABL antibodies. The immunoprecipitates were subjected to in vitro autophosphorylation in the presence of [γ-$^{32}$]ATP and MnCl$_2$. Proteins were analyzed by SDS-polyacrylamide gel electrophoresis, transferred to nitrocellulose and subjected to phosphopeptide mapping. A single phosphopeptide which is present in the wild type P185 protein, but is absent from the mutant P185 (Y177F) protein is indicated by arrows. The experiment shown was been exposed to autoradiography for 16 hr.

Figure 8A:
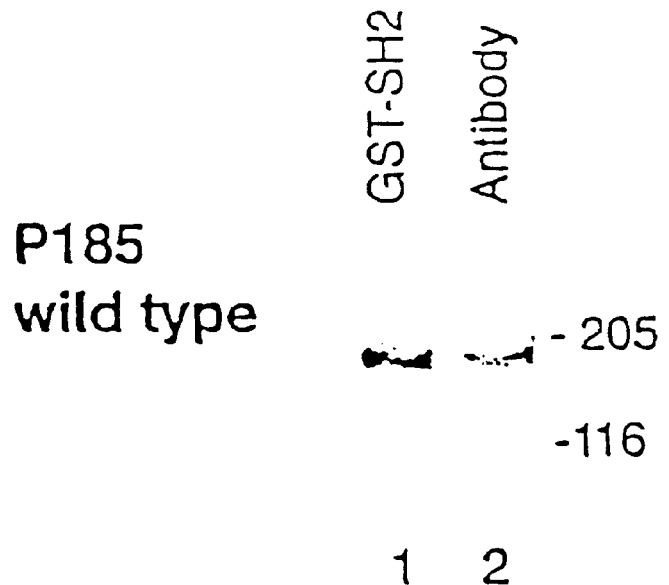

FIG. 8A. Mutation of tyrosine 177 to phenylalanine in the BCR first exon abolishes binding of the GRB-2 SH2 domain to BCR-ABL. Sf9 insect cells were co-transfected with wild type baculovirus DNA and wild type P185 BCR-ABL cDNAs cloned into the pAcC12 vector. Six days post-transfection, the cells were metabolically labeled with [$^{35}$S] methionine. The cells were lysed and the lysates incubated with GST-GRB2 SH2 (lanes 1) or with anti-ABL pEX4 antibodies with protein A-Sepharose beads (lanes 2). The bound proteins were analyzed by SDS 7% polyacrylamide gel electrophoresis and fluorography.

Figure 8B:
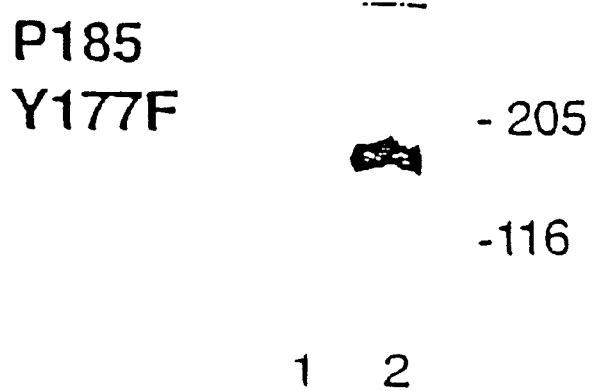

FIG. 8B. Mutation of tyrosine 177 to phenylalanine in the BCR first exon abolishes binding of the GRB-2 SH2 domain to BCR-ABL. Sf9 insect cells were co-transfected with wild type baculovirus DNA and P185 BCR-ABL (Y177F) cDNAs cloned into the pAcC12 vector. Six days post-transfection, the cells were metabolically labeled with [$^{35}$S] methionine. The cells were lysed and the lysates incubated with GST-GRB2 SH2 (lanes 1) or with anti-ABL pEX4 antibodies with protein A-Sepharose beads (lanes 2). The bound proteins were analyzed by SDS 7% polyacrylamide gel electrophoresis and fluorography.

FIG. 9A. Formation of a BCR-ABL-GRB-2 complex in vivo requires the presence of tyrosine 177 in the BCR first exon. COS cells were transfected with P185 wild type (lanes 1–3) and P185 (Y177F) (lanes 4–6), cDNAs cloned into the pSRα MSVtkneo vector. Three days post-transfection, the cells were lysed and the lysates incubated with normal rabbit sera (NRS) (lanes 1 and 4) anti-ABL 2/3 rabbit antibodies (lanes 2 and 5) or anti-GRB-2 antibodies (lanes 3 and 6) for 2 hrs. at 4° C. The immunoprecipitates were collected on protein A-Sepharose beads and subjected to in vitro phosphorylation in the presence of [γ$^{32}$P]ATP and MnCl2. Proteins were analyzed by SDS 10% polyacrylamidegel electrophoresis and autoradiography.

Figure 9B:
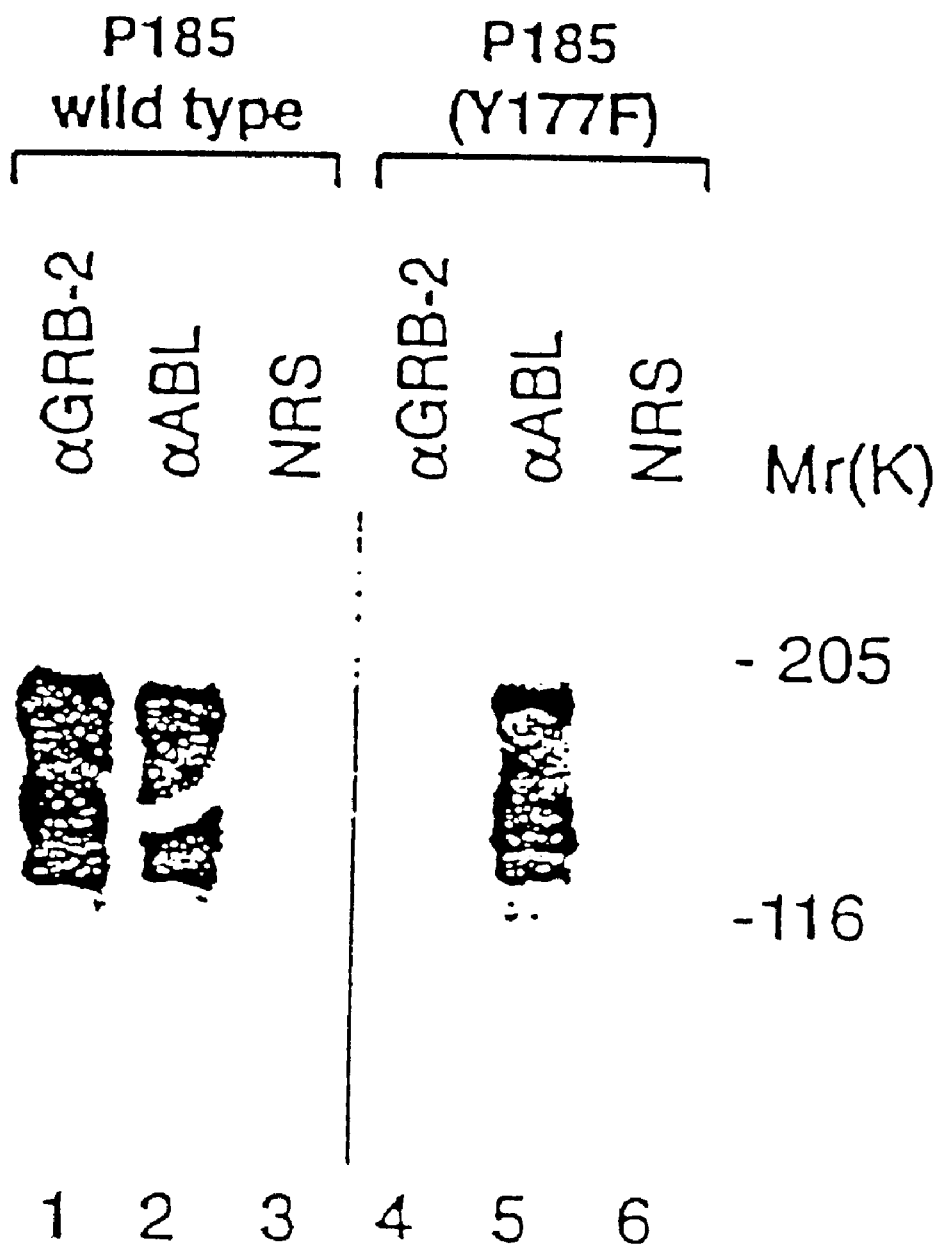

FIG. 9B. Formation of a BCR-ABL-GRB-2 complex in vivo requires the presence of tyrosine 177 in the BCR first exon. Lysates of G418-selected Rat1 cells expressing P185 wild type (lanes 1–3) and P185 (Y177F) (lanes 4–6) were incubated for 2 hrs. at 4° C. with anti-GRB-2 antibodies (lanes 1 and 4), anti-ABL 2/3 antibodies (lanes 2 and 5) or normal rabbit sera (NRS) (lanes 3 and 6). The immunoprecipitates were collected on protein A-Sepharose beads. The bound proteins were analyzed by SDS 10% polyacrylamide gel electrophoresis followed by immunoblotting with anti-ABL mouse monoclonal antibody. Immunoreactive bands were visualized with the ECL detection system (Amersham).

FIG. 10. Mutation of Tyrosine 177 in the BCR-ABL oncogene abolishes GRB2 binding and decreases transforming capacity. Superscript legend:

a Names of the different P185 BCR-ABL forms. The mutated or deleted amino acids are indicated in parenthesis.

b Average frequency of colony formation in agar determined from two plates per assay and four to five independent assays per construct.

c Cells were plated in agar 3 days after infection with helper-free retroviral stocks.

d Cells were selected for 12 to 15 days with G418 (0.5 mg/ml) starting 3 days after infection with helper-free retroviral stocks.

e Number of high density bone marrow cultures exhibiting transformed lymphoid outgrowth over the total of cultures plated. Data represent three separate experiments. In each experiment, cell cultures were set up after infection with the respective retroviral stock.

Figure 11:
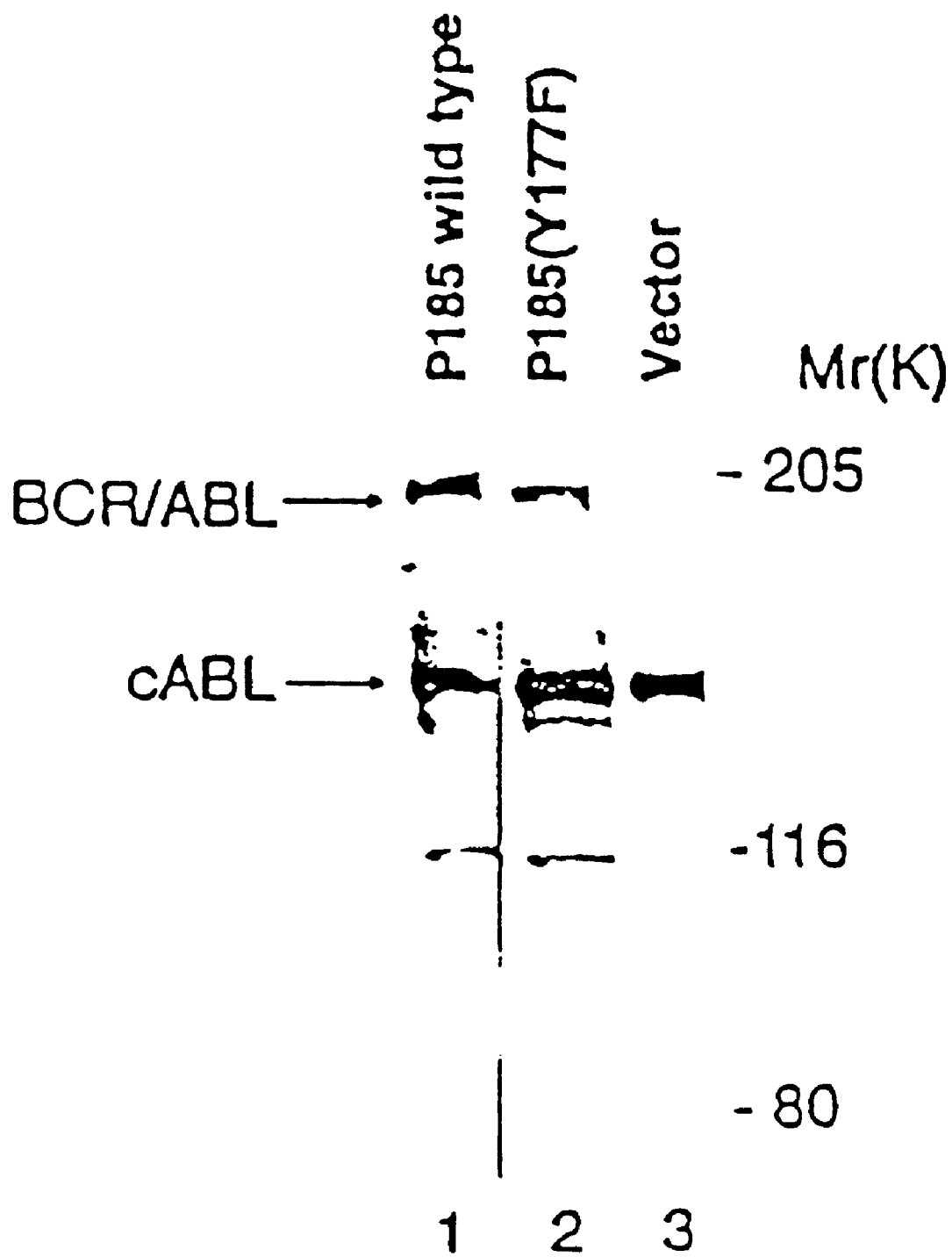

FIG. 11. Expression of wild type and mutant forms of BCR-ABL in Rat1 cells. Rat1 cells were infected with retroviruses encoding for wild type (lane 1) and mutant (Y177F; lane 2) forms of P185 BCR-ABL or vector control (lane 3). Three days post-infection the cells were lysed and subjected to Western blotting with anti-ABL mouse monoclonal antibody. Immunoreactive bands were visualized with the ECL detection system.

Figure 12:
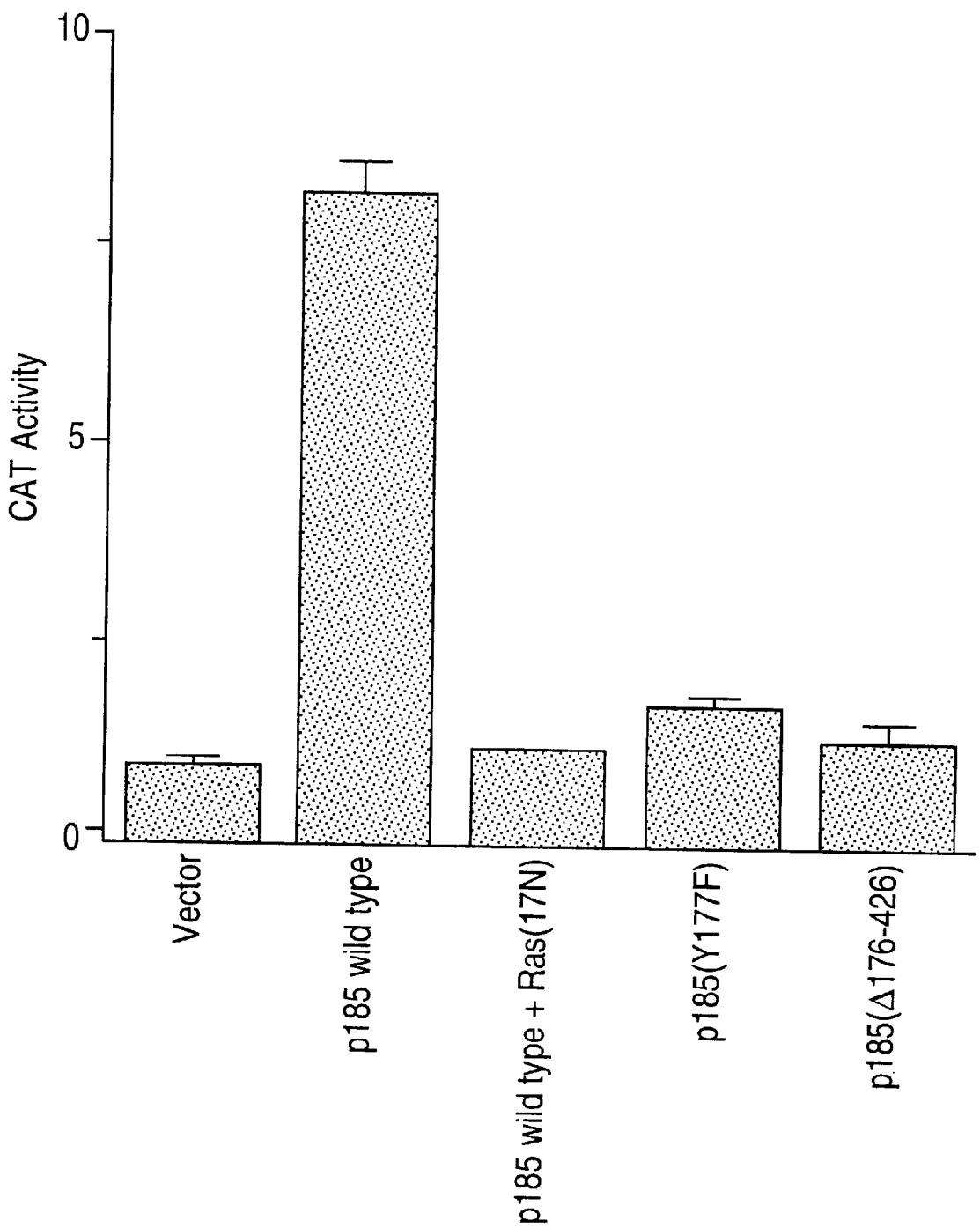

FIG. 12. Stimulation of transcriptional activation by BCR-ABL through Ras requires the presence of tyrosine 177 in the BCR first exon. NIH 3T3 cells were transfected with 0.5 μg of the indicated BCR-ABL cDNA +/–5 μg H-Ras (17N) cDNA, along with the 1 μg pB4X-CAT reporter plasmid. At 48 hr. post-transfection, cells were harvested and assayed for CAT activity as outlined in Section 9.1.1, below. Data were recorded in arbitrary units; the basal signal due to activity of the reporter.

Figure 13:

FIG. 13. Increase in Ras-GTP following infection of Rat1 cells with BCR-ABL retrovirus. Rat1 cells were infected with helper free retroviral stocks for P185 wild type (lane 1) or vector control (lane 2). Two days post infection, the cells were labeled with [$^{32}$P] orthophosphate (0.5 mCi/ml) for 16 hours in phosphate-free medium. The cells were lysed and Ras immunoprecipitated with anti-Ras monoclonal antibody. Guanine nucleotides bound to Ras were dissociated and subsequently separated by thin layer chromatography on PEI-cellulose plates in 0.75M KH2PO4, pH 3.5. The position of GDP and GTP are indicated.

Figure 14A:
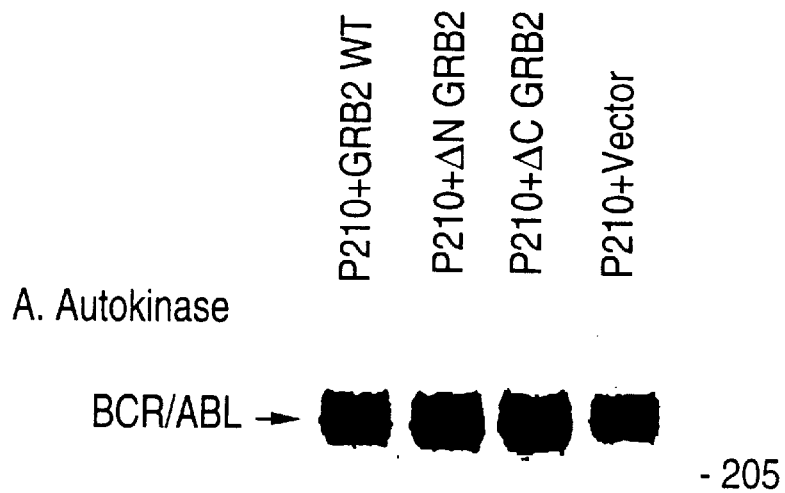

FIG. 14A. Rat1 cells expressing p210 BCR/ABL alone or also expressing wild type GRB2 or a truncated GRB2 were lysed and immunoprecipitated with anti-ABL antibody. Immunoprecipitates were subjected to an in vitro autokiase assay and the samples analyzed by SDS-PAGE (8% gel). No change in ABL kinase activity is seen in cells with elevated GRB2 expression compared to control.

Figure 14B:
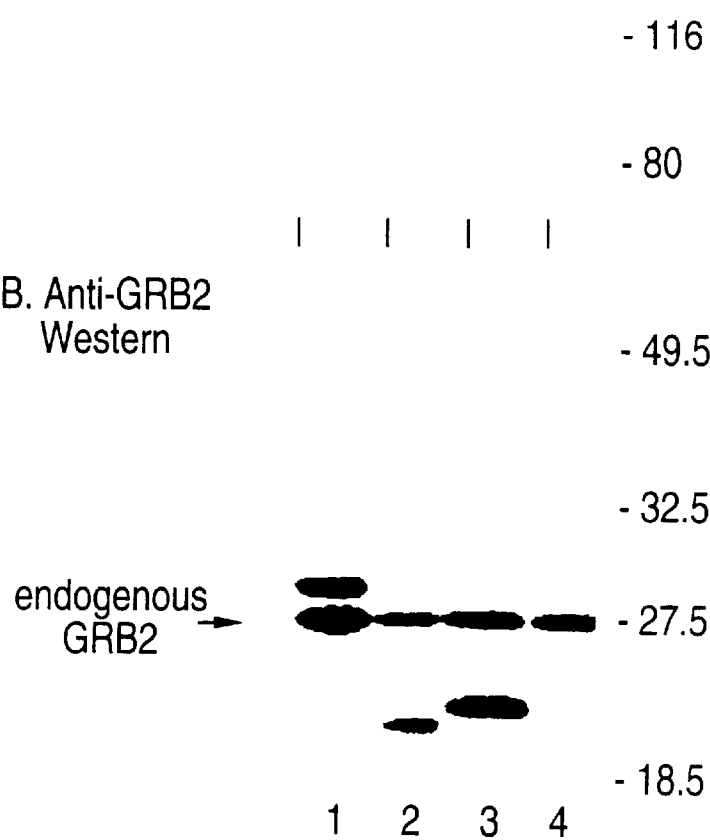

FIG. 14B. Rat1 cells expressing p210 BCR/ABL alone or also expressing wild type GRB2 or a truncated GRB2 were lysed and proteins from the cleared cell lysate were electrophoretically separated using SDS-PAGE (15% gel). Separated proteins were electrophoretically transferred to nitrocellulose filters and then immunoblotted with anti-GRB2 Mab. All GRB2 transformants express approximately the same levels of GRB2 protein.

Figure 15:
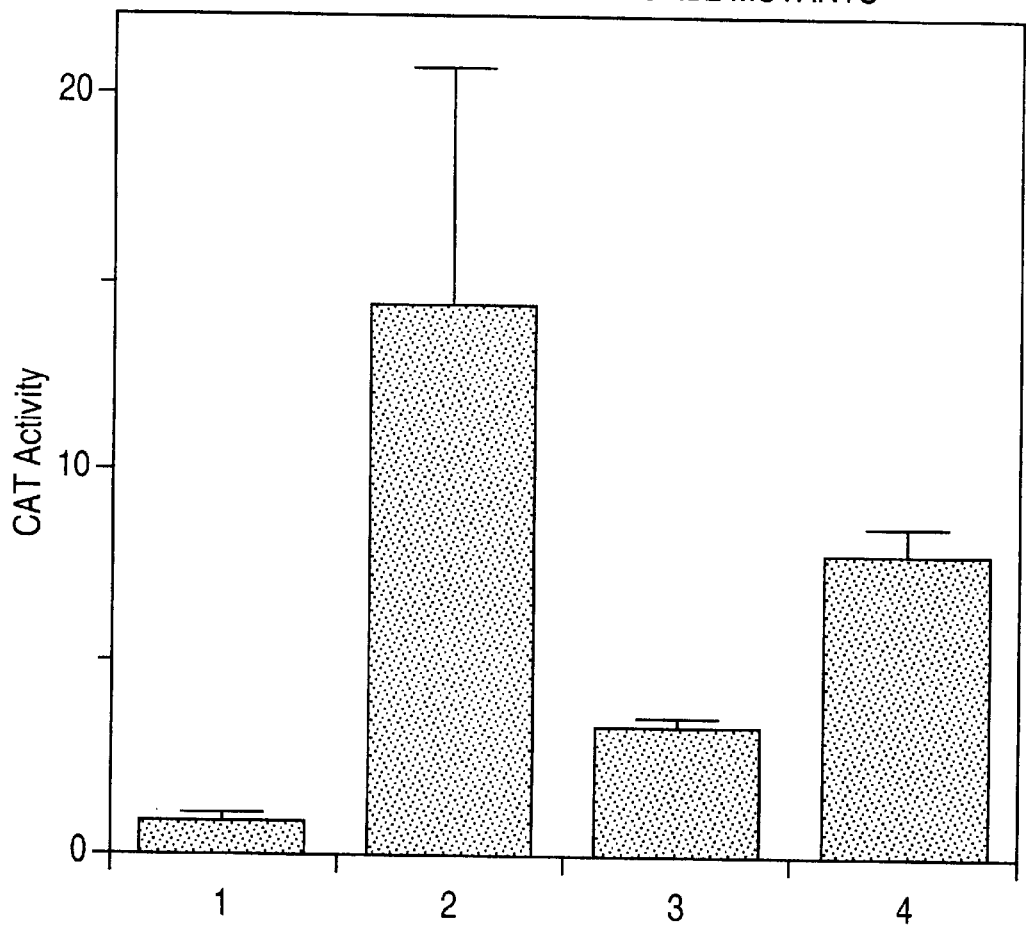

FIG. 15. Stimulation of transcriptional activation by BCR-ABL through Ras requires the presence of a GRB2 SH3 domain. Rat1 cells expressing p210 BCR/ABL cells were transfected with either of the GRB2 deletion mutants, along with the 1 μg pB4X-CAT reporter plasmid. At 48 hr. post-transfection, cells were harvested and assayed for CAT activity as outlined in Section 9.1.1, below. Data were recorded in arbitrary units; the basal signal due to activity of the reporter.

Figure 16:
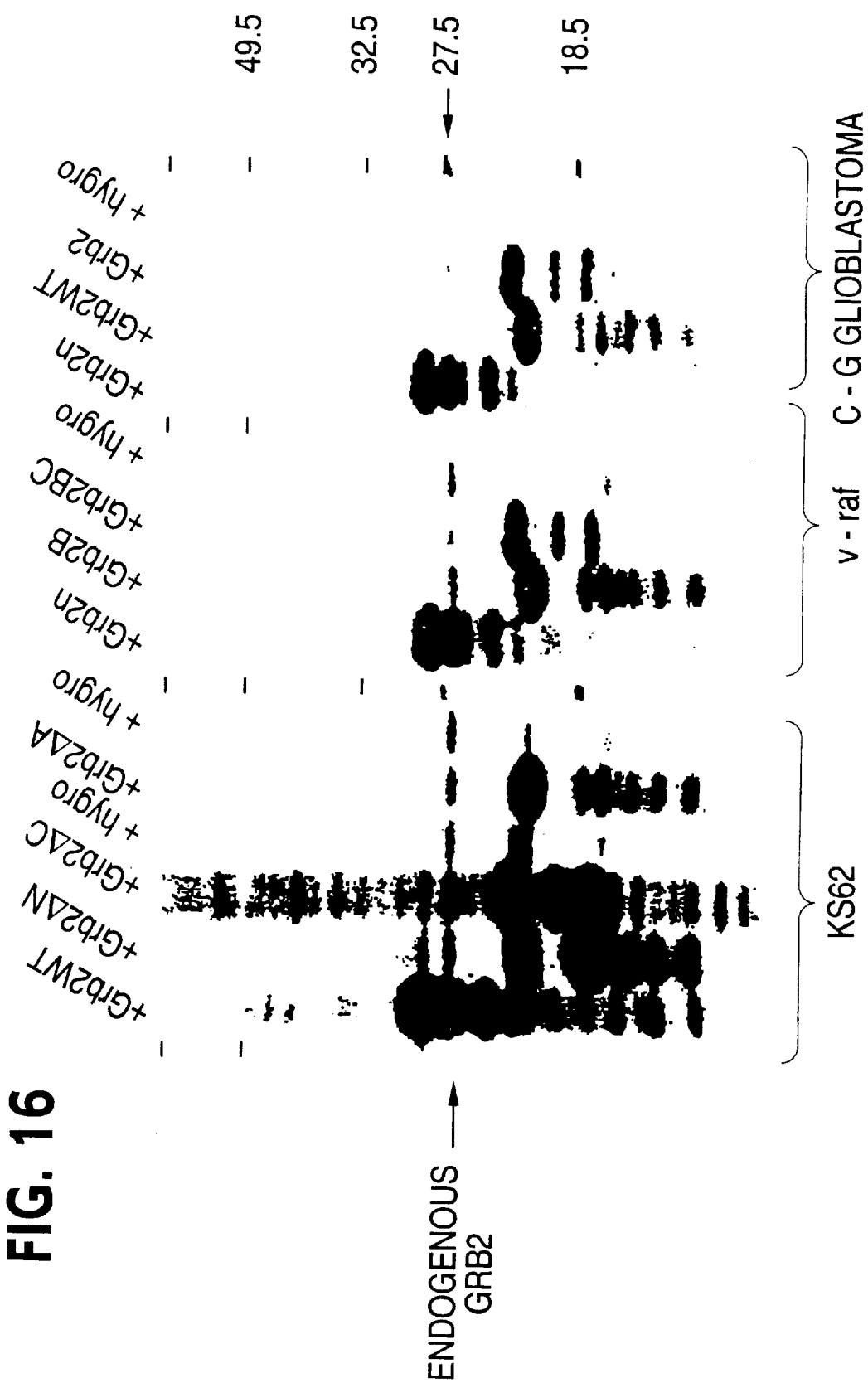

FIG. 16. Lysates were prepared from different GRB2 expressing cell types (K562, Rat 1 cells transfected with v-raf, C-6 gliobastoma) and analyzed by immunoblotting with antibodies to GRB2. The multiple bands represent GRB2 breakdown products.

5. DETAILED DESCRIPTION OF THE INVENTION

Described below are compositions and methods for the prevention and treatment of cell proliferative disorders wherein a protein tyrosine kinase or a protein tyrosine phosphatase capable of complexing with an SH2- and/or SH3-containing member of the adaptor family of proteins is involved. Further, protein tyrosine kinase/adaptor protein complexes, protein tyrosine phosphatase/adaptor protein complexes, methods for the production of such complexes, and uses of these complexes are described herein. Such uses may include, but are not limited to, the identification of agents capable disrupting the interaction between the components of such complexes.

This invention is based, in part, on the surprising discovery that the adaptor protein, GRB-2, binds the intracellular BCR-ABL product in vivo, is necessary for the activation of the oncogenic potential of the BCR-ABL product and that disruption of the GRB-2 signal transduction can reverse the transformed phenotype of cells and reduce tumor growth in animals. The data representing this discovery is presented in the Working Examples of Sections 6 through 12, below.

5.1. Protein Tyrosine Kinase/Adaptor Protein Complexes

The PTK/adaptor protein complexes of the invention comprise at least one member of the PTK family of proteins and at least one member of the adaptor family of proteins, as described below. Under standard physiological conditions, the components of such complexes are capable of forming stable, non-covalent attachments with one or more of the other PTK/adaptor protein complex components.

The PTK components of the PTK/adaptor protein complexes of the invention are either intracellular, cytoplasmic non-receptor PTKs, intracellular, nuclear non-receptor PTKs, or transmembrane, receptor-type PTKs, each of which comprises one or more characteristic peptide domains. Such domains may include one or more catalytic domains which may include, but are not limited to, a tyrosine kinase domain. A tyrosine kinase catalytic domain generally ranges in length from about 250 to about 300 amino acids, corresponding to a molecular weight of approximately 30 kDa. The location of the tyrosine kinase catalytic domain, while not fixed, is generally near the carboxyl terminus of the protein. Short, conserved, stretches of amino acid residues may be present within the tyrosine kinase domain, which alternate in sequence with variable-length stretches of amino acid residues which do not exhibit a high level of conservation. The consensus sequences, corresponding to the most highly conserved of the tyrosine kinase catalytic domain amino acid residues have been compiled and are well known to those of ordinary skill in the art. See, for example, Hanks et al. (Hanks et al., 1991, *Science* 241:42–52), and Wilks (Wilks, A. F., 1990, *Prop. Growth Factor Res.* 2:97–111) which are incorporated herein, by reference, in their entirety.; Among such consensus sequences are the PTK-specific sequences D-L-R-A-A-N (SEQ ID NO:1) or D-L-A-A-R-N (SEQ ID NO:2), and P-I/V-K/R-W-T/M-A-P-E (SEQ ID NO:3). Moreover, see FIG. 1, for a diagram of additional examples of such sequence motifs.

The PTK component of the PTK/adaptor protein complexes of the invention may further include one or more non-catalytic domains, which may include, but are not limited to, one or more SH2 and/or one or more SH3 domains, one or more SH2-binding, and/or one or more SH3-binding peptide domains, and/or (in the case of receptor PTKs) a hydrophobic transmembrane domain. An SH2 (i.e., src homology 2) non-catalytic domain is generally approximately 100 amino acid residues in length. Such SH2 domains may contain a number of highly conserved or invariant amino acid residues within several, preferably five, well-conserved amino acid sequence motifs, which are well known to those of ordinary skill in the art. See, for example Koch et al. (Koch et al., 1991, *Science* 252:668–674), which is incorporated herein, by reference, in its entirety. For example, the amino acid consensus sequences may include, but are not limited to, F-L-I-R-E-S (SEQ ID NO:4) and F-L-V-R-E-S (SEQ ID NO:5). The R residue of these consensus sequences is invariant among SH2 domains. Such well-conserved amino acid sequences motifs are separated by stretches of more variable amino acid sequence elements, which, while variable, generally contain one or more G or P residues.

An SH3 (i.e., src homology 3) non-catalytic domain is approximately 50 amino acids residues in length. While the amino acid sequence within an SH3 domain may be variable, the 3-dimensional, tertiary, structure of the domain is well conserved. Such an SH3 tertiary structure is well known to those of ordinary skill in the art. See, for example, Koyama et al. (Koyama et al., 1993, *Cell* 72:945–952) which is incorporated herein, by reference, in its entirety.

SH2-binding peptide domains are well known in the art. See, for example, Songyang et al. (Songyang et al., 1993, *Cell* 72:767–778), Rotin et al. (Rotin et al., *EMBO J.* 11:559–567), and Skolnick et al. (Skolnick et al., 1993, *EMBO J.* 12:1929–1936), which are incorporated herein, by reference, in its entirety. SH2 domains may exhibit a specificity for certain SH2-binding domains. For example, SH2-binding peptide domains may include, but are not limited to a phosphotyr-hydrophilic-hydrophilic-Ile/Pro amino acid sequence motif (generally,, such a sequence motif is preferred for SH2 domains of the type found in, for example, the src, fyn, lck, fgr, abl, crk, and nck proteins), and phosphoTyr-hydrophobic-X-hydrophobic, and/or phosphotyr-Met-X-Met (generally, such sequence motifs are preferred for SH2 domains of the type found in, for example, p85, phospholipase C-$\gamma$, and SHPTP2 proteins). Further, a consensus sequence developed from the analysis of the domains of several proteins that bind the SH2 domains of the GRB-2 protein has been determined to be X-P-X-Y-V/I-N-V/I (SEQ ID NO:6). In addition, SH2-binding peptide domains may comprise regions rich in Ser and Thr residues some or all of which are phosphorylated (Pendergast et al., 1991, *Cell* 66:161–171).

SH3-binding peptide domains are also well known to those of ordinary skill in the art. See, for example, Ren et al. (Ren et al., 1993, *Science* 259:1157–1161) and Cicchetti et al. (Cicchetti et al., 1992, *Science* 257:803–806), which are incorporated herein, by reference, in their entirety. Such SH3-binding peptide domains are generally rich in Pro amino acid residues, although amino acid residues in addition to solely Pro are also critical for SH3 binding. One possible consensus sequence for a SH3-binding domain is: X-P-X-X-P-P-P-hydrophobic residue-X-P (SEQ ID NO:7). Further, the SH3 domains of GRB-2 have been determined to be P-P-P-V-P-P-R-R (SEQ ID NO:8), an amino acid sequence motif found in the SOS protein (Li et al., 1993, *Nature* 363:8588; Schlessinger, 1993, *TIBS,* 18:273–275.

Intracellular, cytoplasmic PTK components of the PTK/adaptor protein complex of the invention may include, for example, members of the Src family, such molecules as src, yes, fgr, fyn, lyn, hck, lck, and blk; members of the Fes family, such as fes and fer; members of the Abl family, such as abl and arg; and members of the Jak family, such as jak1 and jak2. In a preferred embodiment of the invention, the PTK component of the PTK/adaptor protein complex is the. intracellular PTK product of the BCR-ABL gene. Transmembrane, receptor PTK components of the PTK/adaptor protein complex of the invention may include, for example, such molecules as members of the FGF receptor, Sevenles/ROS, Insulin receptor, PDGF receptor, EGF receptor family of growth factor receptors or any other molecule that associates with he adaptor protein (see for example Lowenstein et al., 1992, *Cell* 70:431–442).

The adaptor protein components of the PTK/adaptor protein complexes of the invention comprise one or more SH2 and/or one or more SH3 non-catalytic domains. The SH2 and SH3 domains which may be a part of the adaptor proteins are as described, above, for the PTK components. Adaptor proteins which may be components of the PTK/adaptor protein complexes of the invention, may include, for example, p85, c-Crk, SHC, Nck, ISGF3$\alpha$, guanine triphosphatase activator protein (GAP), and members of the GRB subfamily of proteins, such as GRB1, GRB-2, GRB-3, GRB-4, GRB-7, and GRB-10. In a preferred embodiment, the PTK/adaptor protein complex of the invention comprises the PTK product of the BCR-ABL gene and GRB-2 protein.

The complexes of the invention, and/or the individual components of the complexes of the invention may be substantially purified utilizing methods which are described below, in Section 5.3.1. Further, the PTK and/or adaptor components of the complexes of the invention may be produced by utilizing a variety of methods which include, but are not limited to, chemical synthesis or recombinant DNA techniques, as described in Section 5.3.2, below.

5.2. Protein Tyrosine Phosphatase/Adaptor Protein Complexes

The PTP/adaptor protein complexes of the invention comprise at least one member of the PTP family of proteins and at least one member of the adaptor family of proteins. Under standard physiological conditions, the components of such complexes are capable of forming stable, non-covalent attachments with one or more of the other PTP/adaptor protein complex components.

The PTP components of the PTP/adaptor protein complexes of the invention are either cytoplasmic, intracellular, non-receptor PTPs or transmembrane, receptor-type PTPs, each of which comprises one or more characteristic peptide domains. Such domains may include one or more catalytic domains which may include, but are not limited to, a tyrosine phosphatase domain. Generally, a tyrosine phosphatase catalytic domain is approximately about 230 amino acids in length. Approximately 40 of the amino acid residues of the catalytic phosphatase domain are highly conserved, and of these, a very highly conserved segment of 11 amino acid residues with the consensus sequence I/V-H-C-X-A-G-X-X-R-S/T-G (SEQ ID NO:9) is generally present. Non-receptor PTPs generally contain a single such catalytic domain, while the transmembrane receptor PTPs generally contain two such catalytic domains separated by a peptide segment approximately 58 amino acid residues in length.

The PTP component of the PTP/adaptor protein complexes of the invention may further include one or more non-catalytic domains, which may include, but are not limited to one or more SH2 domains, one or more SH3 domains, one or more SH2-binding domains, and/or one or more SH3-binding domains. Each of these non-catalytic domains may be as described, above, in Section 5.1.

Transmembrane, receptor PTP components of the PTP/adaptor protein complexes of the invention may include, for example, CD45, LAR, RPTP$\alpha$, RPTP$\beta$, RPTP$\chi$, and RPTP$\kappa$. Intracellular, cytoplasmic PTP components of the PTP/adaptor protein complexes of the invention may include, for example, PTP1C, PTP1D, and corkscrew.

5.3. Purification and Production of PTK/Adaptor and PTP/Adaptor Complexes 5.3.1. Purification Methods The PTK/adaptor and PTP/adaptor complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the PTK/adaptor or PTP/adaptor complex to a combination of standard methods, for example, ammonium sulfate precipitation, molecular sieve chromatography, and/or ion exchange chromatography. Alternatively, or additionally, a PTK/adaptor or PTP/adaptor complex may be purified by immunoaffinity chromatography using an immunoadsorbent column to which an antibody is immobilized which is capable of binding to one or more components of the PTK/adaptor or PTP/adaptor complex. Such an antibody may be of monoclonal or polyclonal in origin. Other useful types of affinity purification for a PTK/adaptor or PTP/adaptor complex may utilize, for example, a solid-phase substrate which binds the catalytic domain (i.e., kinase domain of PTK or phosphatase domain of PTP), or an immobilized binding site for noncatalytic domains of the PTK, PTP, and/or adaptor components of the complex, which bind in such a manner as to not disrupt the complex.

The PTK/adaptor or PTP/adaptor complexes of the present invention may be biochemically purified from a variety of cell or tissue sources. For purification of a naturally occurring PTK/adaptor complex, cellular sources may include, for example, baculovirus-infected SF9 cells, A-431, CHO, and/or 3T3 cells. In a preferred embodiment of the present invention, the PTK/adaptor complex comprises a BCR-ABL PTK and a GRB2 protein. Sources for the purification of such a PTK/GRB-2 complex may include, but are not limited to K562, NMG-01, and ALL-1 cell lines.

5.3.2. Synthesis Methods

Methods for the synthesis of polypeptides or fragments thereof, which are capable of acting as components of the PTK/adaptor or PTP/adaptor complexes of the present invention, are well-known to those of ordinary skill in the art. See, for example, Creighton, 1983, Proteins: Structures and Molecular Principles, W. H. Freeman and Co., N.Y., which is incorporated herein, by reference, in its entirety. Components of a PTK/adaptor or PTP/adaptor complexes which have been separately synthesized or recombinantly produced, may be reconstituted to form a complex by standard biochemical techniques well known to those skilled in the art. For example, samples containing the components of the PTK/adaptor complex may be combined in a solution buffered with greater than about 150 mM NaCl, at a physiological pH in the range of 7, at room temperature. For example, a buffer comprising 20 mM Tris-HCl, pH 7.4, 137 mMNaCl, 10% glycerol, 1% Triton X-100, 0.1% SDS, 0.5% deoxycholate and 2 mM EDTA could be used. Such a procedure may also be utilized for the reconstitution of a PTP/adaptor complex.

Methods for preparing the components of PTK/adaptor complexes of the invention by expressing nucleic acid encoding PTK, PTP, and/or adaptor proteins are described herein. Methods which are well known to those skilled in the art can be used to construct expression vectors containing PTK, PTP, and/or adaptor protein coding sequences and appropriate transcriptional/translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., 1989, Molecular Cloning, A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the coding sequences of the components of the PTK/adaptor PTP/adaptor complexes of the invention. These include but are not limited to, microorganisms such as bacteria (e.g. *E. coli, B. subtilis*) transformed with recombinant bacteriophage DNA, plasmid DNA or cosmid DNA expression vectors containing PTK, PTP, or adaptor protein coding sequences; yeast (e.g. Saccharomyces, Pichia) transformed with recombinant yeast expression vectors containing the PTK, PTP, and/or adaptor protein coding sequences; insect cell systems infected with recombinant virus expression vectors (e.g. baculovirus) containing the PTK, PTP, and/or adaptor protein coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing the PTK, PTP, and/or adaptor protein coding sequences coding sequence; or mammalian cell systems (e.g. COS, CHO, BHK, 293, 3T3) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems a number of expression vectors may be advantageously selected depending upon the use intended for the PTK/adaptor or PTP/adaptor complex being expressed. For example, when large quantities of PTK/adaptor or PTP/adaptor complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, *EMBO J.* 2:1791), in which the PTK, PTP, and/or adaptor protein coding sequence may be ligated individually into the vector in frame with the lac Z coding region so that a fusion protein is produced; pIN vectors (Inouye et al., 1985, *Nucleic Acids Res.* 13:3101–3109; Van-Heeke et al., 1989, *J. Biol. Chem.* 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned PTK and/or adaptor protein can be released from the GST moiety.

In an insect system, *Autographa californica* nuclear polyhidrosis virus (AcNPV) is used as a vector to express foreign genes. The virus grows in *Spodoptera frugiperda* cells. The PTK/adaptor or PTP/adaptor complex component coding sequences may be cloned individually into non-essential regions (for example the polyhedrin gene) of the virus and placed under control of an AcNPV promoter (for example the polyhedrin promoter). Successful insertion of the coding sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g. see Smith et al., 1983, *J. Viol.* 46:584; Smith, U.S. Pat. No. 4,215,051).

In mammalian host cells, a number of viral based expression systems may be utilized. In cases where an adenovirus is used as an expression vector, the PTK/adaptor or PTP/adaptor complex component coding sequences may be ligated to an adenovirus transcription/translation control complex, e.g. the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing PTK, PTP, and/or adaptor proteins in infected hosts. (e.g. see Logan et al., 1984, *Proc. Natl. Acad. Sci. USA* 81:3655–3659). Specific initiation signals may also be required for efficient translation of inserted PTK, PTP, and/or adaptor coding sequences. These signals include the ATG initiation codon and adjacent sequences. In cases where an entire PTK, PTP, or adaptor protein gene, including its own initiation codon and adjacent sequences, is inserted into the appropriate expression vector, no additional translational control signals may be needed. However, in cases where only a portion of the PTK, PTP, or adaptor coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:516–544).

In addition, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc. For long-term, high-yield production of recombinant proteins, stable expression is preferred. For example, cell lines which stably coexpress both the PTK and adaptor protein or PTP and adaptor protein may be engineered. Rather than using expression vectors which contain viral origins of replication, host cells can be transformed with the PTK and adaptor protein DNA or PTP and adaptor protein DNA independently or coordinately controlled by appropriate expression control elements (e.g. promoter, enhancer, sequences, transcription terminators, polyadenylation sites, etc.), and a selectable marker.: Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PTK and adaptor protein or PTP and adaptor protein. Such engineered cell lines are particularly useful in screening and evaluation of compounds that affect signals mediated by the complexes.

A number of selection systems may be used, including but not limited to the herpes simplex virus. thymidine kinase (Wigler et al., 1977, *Cell* 11:223), hypoxanthine-guanine phosphoribosyltransferase (Szybalska et al., 1962, *Proc. Natl. Acad. Sci. USA* 48:2026), and adenine phosphoribosyltransferase (Lowy, et al., 1980, *Cell* 22:817) genes can be employed in tk–, hgprt– or aprt– cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan et al., 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes.

New members of the PTK, PTP, and/or adaptor protein families capable of forming the complexes of the invention may be identified and isolated by molecular biological techniques well known in the art. For example, a previously unknown PTK, PTP, or adaptor protein gene may be isolated by performing a polymerase chain reaction (PCR) using two degenerate oligonucleotide primer pools designed on the basis of highly conserved sequences within domains common to members of the PTK, PTP, or adaptor protein family. The template for the reaction may be cDNA obtained by reverse transcription of mRNA prepared from cell lines or tissue known to express PTK/adaptor and/or PTP/adaptor complexes. The PCR product may be subcloned and sequenced to insure that the amplified sequences represent the sequences of a member of the PTK, PTP, or adaptor subfamily. The PCR fragment may then be used to isolate a full length PTK, PTP, or adaptor protein CDNA clone by radioactively labeling the amplified fragment and screening a bacteriophage cDNA library. Alternatively, the labeled fragment may be used to screen a genomic library. For a review of cloning strategies which may be used, see e.g. Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

A general method for cloning previously unknown adaptor proteins has been described by Skolnick (Skolnick, E. Y., 1991, *Cell* 65:75) and Skolnick et al., (U.S. patent application Ser. No. 07/643,237) which are incorporated herein, by reference, in their entirety. Briefly, new members of the adaptor family of proteins may be identified by their ability to specifically bind to at least a portion of a tyrosine-phosphorylated peptide comprising an adaptor-protein-binding region. Such a region may include, but is not limited to an SH2-binding domain.

5.4. Derivatives of PTK/adaptor and PTP/adaptor Complexes

Also provided herein are functional derivatives of a PTK/adaptor and PTP/adaptor complexes. By "functional derivative" is meant a "chemical derivative," "fragment," "variant," "chimera," or "hybrid" of the PTK/adaptor and PTP/adaptor complex, which terms are defined below. A functional derivative retains at least a portion of the function of the PTK, PTP, or adaptor protein, for example reactivity with an antibody specific for the PTK/adaptor or PTP/adaptor complex, PTK or PTP enzymatic activity or binding activity mediated through noncatalytic domains, which permits its utility in accordance with the present invention.

A "chemical derivative" of the PTK/adaptor or PTP/adaptor complex contains additional chemical moieties not normally a part of the protein. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted. with succinic or other carboxylic acid anhydrides. Derivatization with these agents has the effect or reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'-N-C-N-R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the PTK/adaptor or PTP/adaptor complexes to each other or the PTK/adaptor receptor complex to a water-insoluble support matrix or to other macromolecular carriers. Commonly used cross-linking agents include, for example, 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in Remington's Pharmaceutical Sciences, 1990, 18th ed., Mack Publishing Co., Easton, Pa.

The term "fragment" is used to indicate a polypeptide derived from the amino acid sequence of the PTK, PTP, or adaptor proteins, of the PTK/adaptor or PTP/adaptor complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the PTK, PTP, or adaptor proteins to delete one or more amino acids at one or more sites of the C-terminus, N-terminus, and/or within the native sequence. Fragments of a PTK, PTP, or adaptor protein, when present in a complex resembling the naturally occurring PTK/adaptor or PTP/adaptor complex, are useful for screening for compounds that act to modulate signal transduction, as described below. It is understood that such fragments, when present in a complex may retain one or more characterizing portions of the native PTK/adaptor or PTP/adaptor complex. Examples of such retained characteristics include: catalytic activity; substrate specificity; interaction with other molecules in the intact cell; regulatory functions; or binding with an antibody specific for the native PTK/adaptor or PTP/adaptor complex, or an epitope thereof.

Another functional derivative intended to be within the scope of the present invention is a PTK/adaptor or PTP/adaptor complex comprising at least one "variant" polypeptide (e.g. PTK, PTP, or adaptor) which either lack one or more amino acids or contain additional or substituted amino acids relative to the native polypeptide. The variant may be derived from a naturally occurring PTK/adaptor or PTP/adaptor complex component by appropriately modifying the PTK, PTP, and/or adaptor protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native PTK/adaptor or PTP/adaptor complex, as described above.

A functional derivative of PTK/adaptor or PTP/adaptor complexes comprising PTK, PTP, and/or adaptor proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, *DNA* 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of PTK/adaptor or PTP/adaptor complexes with amino acid deletions, insertions and/or substitutions may be conveniently prepared by direct chemical synthesis, using methods well-known in the art. The functional derivatives of the PTK/adaptor or PTP/adaptor complexes typically exhibit the same qualitative biological activity as the native complexes.

5.5. Antibodies to PTK/Adaptor or PTP/Adaptor Complexes

The present invention further relates to antibodies which are capable of specifically recognizing a PTK/adaptor complex or PTP/adaptor complex or an epitope thereof, or of specifically recognizing an epitope on either the PTK, PTP, or adaptor components of the complex which would not be recognized by the antibody when the PTK, PTP, and/or adaptor component is present separate and apart from the PTK/adaptor or PTP/adaptor complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a PTK/adaptor complex in a biological sample, or, alternatively, as a method for the inhibition of PTK/adaptor complex formation, thus, inhibiting the development of a cell proliferative disorder.

Polyclonal antibodies are heterogeneous populations of antibody molecules derived from the sera of animals immunized with an antigen, such as PTK/adaptor complex, or an antigenic functional derivative thereof. For the production of polyclonal antibodies, various host animals may be immunized by injection with the PTK/adaptor or PTP/adaptor complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler et al. (Kohler et al., *Nature* 256:495–497 (1975) and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo production makes this the presently preferred method. of production.

In addition, techniques developed for the production of "chimeric antibodies" (Morrison et al., 1984, *Proc. Natl. Acad. Sci.,* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively,. techniques described for the production of single chain antibodies (U.S. Pat. No. 4,946,778; Bird, 1988, *Science* 242:423–426; Huston et al., 1988, *Proc. Natl. Acad. Sci. USA* 85:5879–5883; and Ward et al., 1989, *Nature* 334:544–546) can be adapted to produce PTK/adaptor complex-specific or PTP/adaptor complex-specific single-chain antibodies. Single chain antibodies are formed by linking the heavy and light chain fragment of the Fv region via an amino acid bridge, resulting in a single chain polypeptide.

Antibody fragments which contain specific binding sites of a PTK/adaptor or PTP/adaptor complex may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity to the PTK/adaptor or PTP/Adaptor complex.

5.6. Treatment of PTK/Adaptor Protein- and PTP/Adaptor Protein-Related Cell Proliferative Disorders The present invention demonstrates, for the first time, that the binding of a member of the SH2- and/or SH3-containing family of adaptor proteins can represent an essential step in oncogenesis and the transformation process. More specifically, the data presented in the Working Examples in Section 6 through 12, below, detail the binding of the GRB2 member of the GRB subfamily of adaptor proteins to the intracellular PTK product of the human BCR-ABL gene.

Described in this Section are some of the variety of uses to which the binding of such PTKs and adaptor proteins and/or PTPs and adaptor proteins can be put for the treatment of cell proliferative disorders involving such complexes. The uses described herein focus on, but are not limited to, the identification of agents capable of disrupting such complexes (i.e., decreasing or inhibiting the interaction between the component PTK or PTP, and adaptor members of the complexes), and the utilization of such compounds for the treatment of cell proliferative disorders involving a PTK or a PTP capable of complexing with a member of the SH2- and/or SH3-containing family of adaptor proteins. "Disrupting", s used herein, is meant to refer not only to a physical separation of protein complex components, but also refers to a perturbation of the activity of the complexes, regardless of whether or not such complexes remain able, physically, to form. "Activity", as used here, refers to the function of the protein complex in the signal transduction cascade of the cell in which such a complex is formed, i.e., refers to the function of the complex in effecting or inhibiting transduction of an extracellular signal into a cell. Examples of such cell proliferative disorders, include, but are not limited to, oncogenic disorders such as, for example. chronic myelogenous and acute lymphocytic leukemias as well as psoriasis and atherosclerosis. The complexes of the present invention may also be involved in such cellular processes such as activation, differentiation, and survival.

Depending on the individual PTK/adaptor protein complex or PTP/adaptor protein complex, disrupting the interaction between component members of such complexes may have differing modulatory effects on the signal transduction event involved, i.e., the effect of the complex disruption may activate, reduce, or block the signal normally transduced into the cell. Likewise, depending on the cell proliferative disorder involved, either activation, reduction, or blockage of the signal normally transduced into the cell will be desirable for the treatment of the disorder. For example, one effect of the complexing of the BCR-ABL PTK with the GRB-2 adaptor protein causes the activation of the Ras signalling pathway (see the Working Example presented, below, in Section 8). Thus, the disruption of such a BCR-ABL PTK/GRB-2 adaptor protein complex would inhibit the transduction of the abnormal signal and prevent activation of the Ras pathway. Alternatively, a cell proliferative disorder involving a PTK/adaptor or PTP/adaptor complex may, for example, develop because the presence of such complexes brings about the aberrant inhibition of a normal signal transduction event. In such a case, the disruption of the complex would allow the restoration of the usual signal transduction event. Further, an aberrant complex may bring about an altered subcellular adaptor protein localization, which may result in, for example, such dysfunctional cellular events as a cytoskeletal reorganization, as can be the case for the GRB-2 member of the GRB subfamily of adaptor proteins. An inhibition of the PTK/adaptor or PTP-ladaptor complex in this case would allow for restoration or maintenance of a normal cellular architecture. Still further, an agent or agents that cause(s) disruption of the PTK/adaptor or PTP/adaptor complex may bring about the disruption of the interactions among other potential components of such a complex, which may include, but are not limited to an SOS protein.

When considering PTK/adaptor and PTP/adaptor protein complexes wherein the PTK or the PTP component of the complex is a transmembrane, receptor-type PTK or PTP molecule, the receptors or their ligands may be used directly to modulate signal transduction events which may lead to the development of cell proliferative disorders. For example, taking the case of PTKs, soluble PTKs, peptides representing extracellular PTK domains, or peptides representing those portions of extracellular PTK domains which are known to bind ligands may be administered, using techniques well known to those skilled in the art, that, when exposed to the PTK-expressing cells of interest could act to compete with endogenous transmembrane PTK receptor molecules for available ligands, thus reducing or inhibiting ligand binding to endogenous PTKs. The effect of such a procedure could bring about a reduction or inhibition of the interaction between the PTK and the adaptor protein, possibly by blocking the autophosphorylation of the PTK which could, in turn, reduce the affinity of the adaptor protein for the PTK molecule. An analogous situation would hold in the case of PTPs.

In addition, again when considering receptor-type PTKs, extracellular molecules which bind to such PTKs may be administered, using techniques well known to those in the art, which, while binding the PTK do not activate the molecule. Extracellular molecules of this type may be composed, for example, of modified forms of a native ligand for the PTK of interest, such that receptor binding may still occur, but activation of the kinase does not. A molecule with such a design could act in much the same way that administration of soluble PTK would, in that both procedures could have the final effect of reducing or inhibiting the formation of the PTK/adaptor protein complexes. Once again, an analogous situation would occur in the case of the PTPs.

Still further, molecules which are capable of binding native ligands of the receptor PTKs of the PTK/adaptor complexes or the receptor PTPs of the PTP/adaptor complexes of the invention may be administered, using techniques well known to those of skill in the art. Molecules in this class would act to inhibit the ligands' ability to bind it's respective receptor, and thus would have the final effect of reducing or inhibiting the formation of PTK/adaptor or PTP/adaptor protein complexes.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Agents which act intracellularly to directly interfere with the formation of the PTK/adaptor and/or PTP/adaptor complexes of the invention may be administered for the treatment of cell proliferative disorders. Such agents may include, but are not limited to, peptides and/or phosphopeptides comprising SH2 and or SH3 domains, or SH2 and/or SH3-binding domains, small organic molecules or extracts of natural products which would act to compete with the components of the complexes for binding, thus reducing or inhibiting the formation of complexes, which would, in turn, reduce or inhibit the development of the cell proliferative disorder of interest. SH2 and SH3 peptide domains, and SH2-binding and SH3-binding peptide domains are as described, above, in Section 5.1. Such agents may also disrupt the complex by interfering with down stream signaling capability instead of or in addition to complex formation.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Nucleotide sequences encoding the peptide agents which are to be utilized intracellularly may be expressed in the cells of interest, using techniques which are well known to those of ordinary skill in the art. For example, expression vectors derived from viruses such as retroviruses, vaccinia virus, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

Alternatively, antibodies capable of interfering with PTK/adaptor and/or PTP/adaptor complex formation may be administered for the treatment of cell proliferative disorders involving a PTK or PTP capable of forming a complex with an adaptor protein. For example, neutralizing antibodies which are capable of interfering with ligand binding to receptor type PTKs or PTPs may be administered using techniques such as those described above. The effect of such an administration would be similar to that described, above, for the administration of soluble PTKs or PTPS. Additionally, neutralizing antibodies which bind to intracellular epitopes to effect a disruption of PTK/adaptor or PTP/adaptor complex formation may also be administered. Such antibodies may be administered, for example, by utilizing the techniques described above for the administration of agents intended to act intracellularly. Alternatively, nucleotide sequences encoding single-chain antibodies may be expressed within the target cell population by utilizing, for example, techniques such as those described in Marasco et al. (Marasco et al., 1993, *Proc. Natl. Acad. Sci. USA* 90:7889–7893).

The PTK/adaptor complexes and/or PTP/adaptor complexes of the invention may be used to screen for additional molecules that can act to disrupt the activity of the component members of such complexes, and thus may be capable of modulating the signal transduction event such complexes effect. Such compounds may include, but are not limited to, peptides made of D- and/or L-configuration amino acids (in, for example, the form of random peptide libraries; see Lam et al., 1991, *Nature* 354:82–84), phosphopeptides (in, for example, the form of random or partially degenerate, directed phosphopeptide libraries, see Songyang et al., 1993, *Cell* 767–778), antibodies, and small organic molecules.

For example, compounds that bind to individual components, or functional portions of the individual components of the PTK/adaptor or PTP/adaptor complexes (and may additionally be capable of disrupting complex formation) may be identified. A functional portion of an individual component of the complexes may be defined here as a peptide portion of an individual component of a complex still capable of forming a stable complex with another member of the complex. For example, a peptide portion of the SH2-binding domain of a PTK which is still capable of stably binding an SH2 domain of an adaptor protein, and thus is still capable of forming a complex with that adaptor protein. Further, in the case of the catalytic domains of the individual PTK or PTP components of the invention, a functional portion of a catalytic domain may refer to a peptide still capable of stably binding a substrate molecule.

One method utilizing this approach that may be pursued in the isolation of such PTK/adaptor or PTP/adaptor complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. After incubation, unbound compounds are washed away, component-bound compounds are recovered. By utilizing this procedure, large numbers of types of molecules may be simultaneously screened for PTK/adaptor or PTP/adaptor complex component-binding activity.

The PTK/adaptor complex components which may be utilized in the above screening method may include, but are not limited to, PTK molecules or functional portions thereof, such as PTK catalytic domains, phosphorylation domains, SH2 domains, SH3 domains, SH2-binding domains, or SH3-binding domains, and adaptor proteins, or functional portions thereof, such as SH2 domains and SH3 domains. The peptides used may be phosphorylated, e.g. may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific PTK. A functional portion of an SH2 domain may be defined as a peptide comprising at least a portion of an SH2 domain which is capable of specifically binding an SH2-binding domain. Likewise, a functional portion of an SH3 domain may be defined as a peptide comprising at least a portion of an SH3 domain which is capable of specifically binding an SH3-binding domain. A functional portion of an SH2-binding domain may be defined as a peptide capable of binding an SH2 domain, and may be at least about 4 amino acid residues in length. A functional portion of an SH3-binding domain may be defined as a peptide capable of binding an SH3 domain, and may be at least about 4 amino acids in length, with a length of about 1 amino acid residues being preferred.

The PTP/adaptor complex components which may be utilized in the above screening method may include, but are not limited to, PTP molecules or functional portions thereof, such as PTP catalytic domains, phosphorylation domains, SH2 domains, SH3 domains, SH2-binding domains, or SH3-binding domains, and adaptor proteins, or functional portions thereof, such as SH2 domains and SH3 domains. The peptides used may be phosphorylated, e.g. may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined asia peptide capable of being specifically phosphorylated at certain amino acids by a specific PTK.Functional portions of SH2, SH3, SH2-binding, and SH3-binding domains may be as described above.

Molecules exhibiting binding activity may be further screened for an ability to disrupt PTK/adaptor or PTP/adaptor complexes. Alternatively, molecules may be directly screened for an ability to disrupt PTK/adaptor or PTP/adaptor complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound.

Additionally, in vivo complex formation may be assayed by utilizing co-immunoprecipitation techniques well known to those of skill in the art. Briefly, a cell line capable of forming a PTK/adaptor or PTP/adaptor complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

The effect of an agent on the transformation capability of the PTK/adaptor or PTP/adaptor complex of interest may be directly assayed. Such agents may but are not required to, include those agents identified by utilizing the above screening technique. For example, an agent or agents may be administered of a cell such as a fibroblast or hematopoietic cell capable of forming a PTK/adaptor complex which, in the absence of any inhibitory agent, would lead to the cell's transformation (Muller et al., 1991, *Mol. Cell. Biol.* 11:1785–1792; McLaughlin et al.,, 1987, *Proc. Natl. Acad. Sci. USA* 84:6558–6562). The transformation state of the cell may then be measured in vitro, by monitoring, for example, its ability to form colonies in soft agar (Lugo et al., 1989, *Mol. Cell. Biol.* 9:1263–1270; Gishizky et al., 1992, *Science* 256:836–839). Alternatively, a cell's transformation state may be monitored in vivo by determining its ability to form tumors in immunodeficient nude on severe combined immunodeficiency (SCID) mice (Sawyers et al., 1992, *Blood* 79:2089–2098). Further, in the case of BCR-ABL, an agent or agents may be administered to animal models of ALL and/or CML which are well known to those of ordinary skill in the art (Gishizky et al., 1993, *Proc. Natl. Acad. Sci. USA* 90:3755–3759) and/or reverse the progress of this oncogenic disorder.

Agents capable of disrupting PTK/adaptor and/or PTP/adaptor complex formation and capable of reducing or inhibiting cell; proliferative disorders which arise from the formation of such complexes may be used in the treatment of patients exhibiting or at risk for such disorders. A sufficient concentration of an agent or agents such as those described above may be administered to a patient so that the cell proliferative capability of cells which, in the absence of such agents, would contain PTK/adaptor and/or PTP/adaptor protein complexes, is reduced or eliminated.

Alternatively, in the case of hematopoietic cell proliferative disorders, such as leukemias, rather than direct administration to the patient, the agent or agents may be used in conjunction with autologous bone marrow transplantation and chemoradiotherapy techniques, which are well known to those of skill in the art. Briefly, an aliquot of bone marrow cells, generally taken from the pelvis, are removed from the patient. The cells are then cultured in the presence of a concentration of agent or agents which is capable of effectively disrupting PTK/adaptor or PTP/adaptor complex. By blocking the signal transduction pathway of those bone marrow cells capable of forming such complexes, one selects against the presence of clonal descendants of these cells, thus effectively purging the cultures of those cells responsible for the hematopoietic cell proliferative disorder being treated. While the bone marrow cells are being cultured and purged of cells with a high oncogenic capacity, the patient is treated with chemoradiotherapy appropriate for the disease involved, using techniques and doses well known to those of skill in the art. Upon completion of such chemoradiotherapy treatment, the patient receives an autologous infusion of the cultured bone marrow cells, which have been purged of oncogenic cells.

In a preferred embodiment of the invention, a PTK/adaptor complex is disrupted or prevented and is one in which the PTK component is an intracellular PTK product of the human BCR-ABL gene, and the adaptor protein component is a GRB-2 member of the GRB subfamily of adaptor proteins. Further, the cell proliferative disorders which administration of such agents treats, in this preferred embodiment include, but are not limited to, chronic myelogenous leukemia and acute lymphocytic leukemia.

6. EXAMPLE
BCR-ABL Associates with GRB-2 Both in vitro and in vivo

In the Working Example presented in this section, it is demonstrated that the GRB-2 member of the GRB subfamily of adaptor proteins binds to the BCR-ABL intracellular PTK both in vitro and in vivo.

6.1. Materials and Methods 6.1.1 Cells and Viruses

*Spodoptera frugiperda* (Sf9) insect cells were propagated in complete Grace's media (Smith, G. E., 1983, *Mol. Cell. Biol.* 3:2156–2165). The Ph[1]-positive leukemic cell lines K562 and NMG-01 were derived from patients with chronic myelogenous leukemia and express P210 BCR-ABL. The PH[1]-positive cell line, ALL-1, was derived from a patient with acute lymphocytic leukemia and expresses P185 BCR-ABL. The PH[1]-positive cell lines were cultured in RPMI 1640 medium with 10% fetal calf serum. COS African green monkey cells and Rat1 fibroblasts were grown in DMEM medium with 5% fetal calf serum.

Recombinant baculoviruses for expression of cBCR, cABL and BCR-ABL were prepared by cotransfecting the corresponding cDNAs cloned into the pAcCI2 baculovirus vector in the presence of wild type baculovirus DNA as described (Pendergast et al., 1991, *Cell* 66:161–171; Pendergast et al., 1991, *Proc. Natl. Acad. Sci. USA* 88:5927–5931).

Helper-free retroviral stocks were prepared by transient hyperexpression in COS cells according to methods previously described (Muller et al., 1991, *Mol. Cell. Biol.* 11:1785–1792). Retroviral stocks were characterized according to their ability to transfer wild type and mutant forms of the BCR-ABL gene product to Rat1 fibroblasts using immunohistochemical methods (Muller et al., 1991, *Mol. Cell. Biol.* 11:1785–1792). Endogenous levels of rat c-abl protein were not detected in these staining procedures. The level of gene transfer was further evaluated by measuring levels of BCR-ABL protein expression (Western blot). Only retroviral stocks showing comparable levels of gene transfer were used in these studies. Titers were in the range of 105 infectious particles per ml as determined by the frequency of G418 resistant Rat1 colonies following exposure to limiting dilutions of the viral stocks.

6.1.2. Antibodies

Polyclonal rabbit antibodies directed against the amino terminus of cBCR, and amino- and carboxy-terminal sequences of cABL have been previously described (Pendergast et al., 1991, *Cell* 66:161–171; Konopka et al., 1984, *Cell* 37:1035–1042). A mouse monoclonal anti-ABL (21–63) antibody was employed for immunoblotting (Pendergast et al., 1991, *Proc. Natl. Acad. Sci. USA* 88:5927–5931). Polyclonal rabbit antibodies to the C-terminal SH3 domain of GRB-2 (Ab50) and to a synthetic peptide derived from the N-terminal SH3 domain of GRB-2 (Ab86) were used for immunoprecipitation and immunoblotting, respectively (Lowenstein et al., 1992, *Cell* 70:431–442).

6.1.3. Plasmid Constructions

The 650-base pair human GRB-2 CDNA (Lowenstein et al., 1992, *Cell* 70:431–442; Matuoka et al., 1992, *Proc. Natl. Acad. Sci. USA* 89:9015–9019) was cloned from a human placenta cDNA library by polymerase chain reaction (PCR) as (5') SH3-SH2 and (3') SH3 fragments. A unique KpnI site at codon 154 of GRB-2 was employed to generate the full length GRB-2 cDNA. The entire coding sequence of GRB-2 and the (3') SH3 domain of GRB-2 were subcloned in-frame into the Bam HI site of the pGEX-2T vector (Pharmacia). The isolated (5') SH3 and SH2 domains of GRB-2 were prepared as described (Skolnik et al., 1993, *EMBO J.* 12:1929–1936).

Preparation of cDNAs for wild type P185 BCR-ABL (McLaughlin et al., 1989, *Mol. Cell. Biol.* 9:1866–1874) and P185 (Δ176–426) (Muller et al., 1991, *Mol. Cell. Biol.* 11:1785–1792) and cloning of the corresponding CDNAs into pSRα (Pendergast et al., 1991, *Proc. Natl. Acad. Sci. USA* 88:5927–5931) and pSRα MSVtKneo (Muller et al., 1991, *Mol. Cell. Biol.* 11:1785–1792) vectors was performed as previously described. The P185 BCR-ABL (Y177F) mutant was created by oligonucleotide-site directed mutagenesis using the Muta-Gene Phagemid in vitro mutagenesis system (Bio Rad). Template was generated by subcloning a 1.6 Kb EcoRI-SacI fragment of cBCR from pGEM4/cBCR into the EcoRI and SacI sites of the pBlueScript SK+ vector (Stratagene) and rescuing the single stranded DNA by coinfecting XL-1 Blue bacteria with the helper phage R408 (Stratagene). The mutagenic oligonucleotide, 5'-AAG CCC TTC TTC GTT AAC GTC GAG-3' (SEQ ID NO: 10), was employed to create a phenylalanine codon in place of tyrosine, by changing nucleotide 530 from an A to a T. In addition, a silent base change at nucleotide 534 was introduced to create a unique HpaI site. Mutagenized plasmids were selected for the presence of the unique HpaI site. The mutations were verified by dideoxy chain termination sequence analysis in both directions. The mutated BCR sequence was introduced into the wild type P185 BCR-ABL cDNA. P185 BCR-ABL (Y177F) was subcloned into the pSRα and pSRα MSVtK-neo mammalian expression vectors and the AcC12 vector for baculovirus expression. Cloning of the cDNA for wild type cABL into the pSRα vector has been previously described (Pendergast et al., *Proc. Natl. Acad. Sci. USA* 88:5927–5931). BCR (Δ872–1271) as also cloned into pSRα as described (Pendergast et al., 1991, *Cell* 66:161–171).

6.1.4. Expression and Purification of GST-Fusion Proteins

GST-fusion proteins were expressed and purified using glutathione-Sepharose 4B beads (Pharmacia) as previously described (Pendergast et al., 1991, *Cell* 66:161–171). Fusion proteins were left on the resin and stored at 4° C.

6.1.5. Metabolic Labeling and Immunoprecipitation

Sf9 cells were infected with the indicated recombinant baculbviruses. Three days post-infection the cells were incubated with 0.1 mCi/ml [$^{35}$S] methionine (ICN) in methionine-free media for 4 to 6 hrs at 27° C. Labeled cells were lysed with either KLB (10 mM sodium phosphate pH 7.0, 150 mM NaCl, 1% Triton X-100) or PCLB (50 mM HEPES, pH 7.0, 150 mm NaCl, 1 mM MgCl$_2$, 1% Triton X-100, 10% glycerol) supplemented with 5 mM EDTA, 1 mM PMSF, 50 μg/ml leupeptin, 25 μg/ml aprotinin, 25 mM NaF, 1 mM NA$_3$VO$_4$, and 0.1 mM Na$_2$MoO$_4$. The lysates were clarified by centrifugation at 100,000×g for 1 hour. Lysates were incubated with the indicated antibodies directly or after a 3-fold dilution with Incubation Buffer (20 mM HEPES, pH 7.0, 150 mM NaCl, 0.1% Triton X-100, 10% glycerol, 0.5 mM Na3VO4, 0.1 mM Na$_2$MoO$_4$, 25 mM NaF, ImM PMSF, 25 μg/ml leupeptin) as indicated. Immune complexes were collected by incubation with Protein A-Sepharose beads (Pharmacia) for 120 minutes at 4° C. The beads were washed extensively with Incubation buffer to remove unbound material. Bound proteins were analyzed by SDS-polyacrylamide gel electrophoresis and visualized by fluorography. Whenever unlabeled lysates were employed, the proteins were detected by immunoblotting with the indicated antibodies.

6.1.6. Binding Assays

Protein lysates were diluted 3-fold with Incubation Buffer and incubated with GST or GST-fusion proteins attached to glutathione-Sepharose beads. After incubation for 90 min. at 4° C., the beads were washed extensively with Incubation Buffer or with RIPA buffer (20 mM Tris-HCl, pH 7.4, 137 mM NaCl, 10% glycerol, 1% Triton X-100, 0.1% SDS, 0.5% deoxycholate and 2 mM EDTA), as indicated. Bound proteins were analyzed by SDS-polyacrylamide followed by fluorography for radiolabelled proteins.

6.1.7. Immunoblotting, in vitro Autophosphorylation and Dephosphorylation Reactions Procedures for immunoblotting and in vitro labeling with [γ$^{32}$P]ATP were carried out essentially as previously described (Pendergast et al., 1991, *Cell* 66:161–171; Pendergast et al., 1991, *Proc. Natl. Acad. Sci. USA* 88:5927–5931). Dephosphorylation with potato acid phosphatase was performed as described (Pendergast et al., 1991, *Cell* 66:161–171; Pendergast et al., 1991, *Proc. Natl. Acad. Sci. USA* 88:5927–5931).

6.2. Results 6.2.1. BCR-ABL Associates with GRB-2 in vivo

To determine whether the BCR-ABL tyrosine kinase forms a physical complex with the GRB-2 adaptor protein in intact cells, it was examined whether the two proteins co-immunoprecipitate. Cell lysates were prepared from the Ph$^1$-positive leukemic cell lines K562, MEG-01, and ALL-1, and were subjected to immunoprecipitation with anti-ABL, anti-GRB-2, or control antibodies. Following extensive washing, the immunoprecipitates were incubated in the presence of radioactive ATP under conditions that promote autophosphorylation of the BCR-ABL kinase. Comparable levels of BCR-ABL protein were precipitated using either anti-GRB-2 or anti-ABL antibodies (FIG. 2, lanes 1–9). Both forms of BCR-ABL, P210 and P185, associated with GRB-2 in Rat1 fibroblasts expressing the corresponding BCR-ABL proteins (FIG. 2, lanes 10–15). Similarly, immunoprecipitation with anti-GRB-2 can be precipitated by anti-ABL antibodies in cell lines where BCR-ABL is expressed (FIG. 3). Metabolic labelingl of the BCR-ABL expressing cells with $^{35}$S-methionine followed by immunoprecipitation with anti-ABL or anti-GRB-2 antibodies demonstrated that 50% to 90% of the BCR-ABL kinase available in the cell is complexed with GRB-2 in agreement with the results shown in FIG. 2. Interestingly, no association of GRB-2 with the oncogenic v-abl kinase (FIG. 2, lanes 16–18) was observed. These experiments demonstrate that the GRB-2 adaptor protein forms a stable complex with both forms of the BCR-ABL tyrosine kinase but not the v-abl kinase and that the BCR-ABL/GRB-2 complexes remain intact following in vitro phosphorylation of BCR-ABL.

6.2.2. BCR-ABL Binds to GRB-2 in vitro

To examine the molecular basis for the association of BCR-ABL with GRB-2, the full-length GRB-2cDNA sequence was cloned into pGEX-2T for expression in bacteria as a glutathione S-transferase (GST) fusion protein. The GST-GRB-2 protein was purified and tested for its ability to bind to BCR-ABL in vitro. It was found that P185 BCR-ABL, expressed in baculovirus-infected insect cells, bound to full length GRB-2 immobilized on glutathione-sepharose beads (FIG. 4, lane 2). No binding to GST alone was detected (FIG. 4, lane 1). The complex of BCR-ABL and GST-GRB-2 remained intact after washing with buffer containing the detergents SDS and deoxycholate (FIG. 4, lane 2).

To identify which GRB-2 domain(s) bind to BCR-ABL, GST fusion proteins were prepared that contained the isolated GRB-2 SH3 and SH2 domains. BCR-ABL bound to the GST-GRB-2 SH2 fusion protein (FIG. 4, lane 4). GST fusion proteins containing the amino- and carboxy-terminal SH3 domains of GRB-2 also bound to the baculovirus-produced BCR-ABL protein in vitro (FIG. 4, lanes 3 and 5). The interaction of BCR-ABL with the SH2 and SH3 domains of GRB-2 was resistant to washing with a buffer containing SDS and deoxycholate (FIG. 4, lanes 3–5). Treatment of BCR-ABL with potato acid phosphatase completely eliminated its ability to associate with the GRB-2 SH2 domain, but did not affect its binding to the GRB-2 SH3 domains.

7. EXAMPLE

BCR-ABL Sequences Necessary for BH2-Mediated Binding of GRB-2 to BCR-ABL

In the Working Example presented in this section, amino acid sequences necessary for BCR-ABL/GRB-2 binding via the GRB-2 SH2 domains are investigated. Specifically, it is demonstrated that binding requires the presence of Tyr-phosphorylated amino acid residues, and further, it is shown that a BCR first exon mutation is capable of abolishing the SH2-mediated BCR/GRB-2 binding.

7.1. Materials and Methods

The materials and techniques utilized in the experiments presented in this Working Example are as those described in Section 6.1, above.

7.2. Results

7.2.1 SH2-Mediated Binding of GRB-2 to BCR-ABL Requires Tyrosine Phosphorylation of BCR Sequences To identify which regions in BCR-ABL participate in GRB-2-binding, BCR and ABL sequences were expressed separately in baculovirus-infected insect cells and tested for their ability to bind to full length GRB-2 as well as to the isolated GRB-2 SH2 and SH3 domains. Baculovirus-produced cABL bound to full length GRB-2 in vitro (FIG. 5, lane 2) but not to the GRB-2 SH2 domain alone (FIG. 5A, lane 4). cABL hyperexpressed in insect cells is phosphorylated on tyrosine residues (Pendergast et al., 1991, *Proc. Natl. Acad. Sci. USA* 88:5927–5931). Thus, the inability of the GRB-2 SH2 domain to bind to the baculovirus-produced cABL protein was not due to lack of tyrosine phosphorylation.

The binding of cABL to GRB-2 in vitro appears to be mediated exclusively via the amino- and carboxy-terminal SH3 domains of GRB-2 (FIG. 5A, lanes 3 and 5). SH3 domains bind to specific proline-rich motifs (Cicchetti et al., 1992, *Science* 257:803–806; Ren et al., 1993, *Science* 259:1157–1161). Recently, it has been shown that GRB-2 binds to the Sosl guanine nucleotide exchanger through the direct interaction of the GRB-2 SH3 domains with the proline-rich sequence, PPPVPPR, present in the carboxy-terminal region of Sosl (Li et al., 1993, *Nature* 363:85–87; Rozakis-Adcock et al., 1993, *Nature* 363:83–85). The carboxy-terminus of cABL contains several proline-rich stretches. However, no PPPVPPR sequence is found in the cABL protein. Binding of the GRB-2 SH3 domains to cABL in vitro is significantly reduced but not completely eliminated in a cABL deletion mutant protein that lacks the majority of the cABL carboxy-terminal domain. These data together with the lack of detectable association between normal cABL and GRB-2 following immunoprecipitation from cell lysates (see FIG. 6A, below), suggest that the cABL/GRB-2 interaction observed in vitro is not specific and may not occur in vivo. However, it ismpossible that the proline-rich domain in cABL serves as binding sites for other SH3 domains.

A similar analysis of the binding of cBCR to full length or isolated domains of GRB-2 in vitro revealed that only the full length GRB-2 and to a lesser extent the N-terminal SH3 domain of GRB-2 bound to cBCR in vitro (FIG. 5B, lanes 2 and 3). Interestingly, no binding of cBCR to the SH2 domain of GRB-2 was detected (FIG. 5B, lane 4).

The complete lack of in vitro binding of the GRB-2 SH2 domain to cABL and CBCR contrasts with the strong binding of this domain to the chimeric BCR-ABL tyrosine kinase (compare FIG. 4 with FIGS. 5A and 5B, lanes 4). The phosphorylation state of cBCR sequences is different in the full length cBCR protein versus the BCR-ABL chimera. The cBCR protein is phosphorylated only on serine/threonine residues in all cell types examined even following hyper-expression in insect cells (Timmons et al., 1989, *Oncogene* 4:559–567; Pendergast et al., 1991, *Cell* 66:161–171). In contrast, in the BCR-ABL chimera, the activated ABL kinase phosphorylates BCR first exon sequences on tyrosine (Liu et al., 1993, *Oncogene* 8:101–109). To evaluate whether tyrosine-phosphorylation of BCR sequences could uncover binding to the isolated GRB-2 SH2 domain, insect cells were co-infected with baculoviruses coding for the full length cBCR and cABL proteins. Trans-phosphorylation of cBCR by the cABL tyrosine kinase resulted in binding of the GRB-2 SH2 domain to cBCR (FIG. 5C, lane 4). Western blotting, with antiphosphotyrosine antibodies demonstrated that CBCR was tyrosine-phosphorylated in Sf9 cells co-infected with cABL and CBCR baculoviruses. A low level of binding of cBCR to the isolated amino- and carboxy-terminal SH3 domains of GRB-2 in vitro was also detected (FIG. 5C, lanes 3 and 5). These results demonstrate that binding of the GRB-2 SH2 domain to BCR sequences requires tyrosine phosphorylation.

7.2.2. GRB-2 Interacts with BCR-ABL but not cABL and CBCR Sequences in vivo To examine whether the in vitro binding of GRB-2 to cABL and cBCR also occurred in vivo, COS cells were transfected with expression constructs of the corresponding cDNAs. Transfection of these cDNAs results in an approximately 50- to 200-fold increase. in the expression of cABL and cBCR over the corresponding endogenous protein levels (Pendergast et al., 1991, *Proc. Natl. Acad. Sci. USA* 88:5927–5931). Under these conditions, no appreciable levels of cABL co-immunoprecipitated with GRB-2 (FIG. 6A, lane 6). Similarly, no interaction of GRB-2 with BCR sequences could be detected following hyperexpression of the BCR sequences retained in the P210 BCR-ABL chimera in COS cells (FIG. 6B, lane 3). In contrast, significant levels of P185 BCR-ABL were precipitated by the anti-GRB-2 antibodies in the same experiment (FIG. 6A, lane 3).

These data, together with the lack of detectable endogenous cABL and CBCR proteins in anti-GRB-2 immuno-precipitates from normal cells, supports the contention that no cABL/GRB-2 and cBCR/GRB-2 complexes may be found in vivo. These findings demonstrate that the BCR-ABL chimera exhibits novel protein binding. properties which are distinct from those of its BCR and ABL protein sequence components.

7.2.3. A Point Mutation in the BCR First Exon Abolishes Binding of The GRB-2 SR2 Domain to BCR Binding of SH2 domains to specific tyrosine-phosphorylated proteins is dependent on the primary sequence C-terminal to the phosphorylated tyrosine (Fanti et al., 1992, *Cell* 69:413–423; Kashishian et al., 1992, *EMBO J.* 11:1373–1382; Sonyang et al., 1993, *Cell* 72:767–778). Examination of the sequences surrounding the eleven potential tyrosine phosphorylation sites within the first exon of BCR revealed that tyrosine 177 is found within the sequence YVNV, which corresponds to an optimal binding site for the GRB-2 SH2 domain (Sonyang et al., 1993, *Cell* 72:767–778; Skolnik et al., 1993, *EMBO J.* 12:1929–1936). Sequences surrounding the other ten tyrosines in the BCR first exon do not conform to optimal binding sites for the GRB-2 SH2 domain or other SH2 domains examined (Sonyang et al., 1993, *Cell* 72:767–778). To determine whether tyrosine 177 is required for the binding of BCR-ABL to the GRB-2 SH2 domain, phenylalanine was substituted for tyrosine 177 in BCR-ABL by site-directed mutagenesis, the mutated protein was expressed in insect cells and was tested for binding to GRB-2. Comparison of the phosphopeptide map patterns of the P185 (Y177F) mutant and P185 wild type proteins following in vitro autophosphorylation revealed the absence of at least one major phosphopeptide in P185 (Y177F) (FIG. 7). Binding studies demonstrated that in contrast to the wild type P185 BCR-ABL, the P185 BCR-ABL (Y177F) mutant protein did not interact with the GRB-2 SH2 domain in vitro (FIG. 8B, lane 1).

Next, the ability of the P185 BCR-ABL (Y177F) mutant to interact with GRB-2 in vivo was evaluated. P185 (Y177F) did not interact with endogenous GRB-2 when hyperexpressed in COS cells (FIG. 9A, lane 6), or in Rat1 fibroblasts that stably express the mutant protein (FIG. 9B, lane 4). Similarly, BCR-ABL deletion mutants which lack tyrosine 177 failed to bind GRB-2. These data indicate that interaction between BCR-ABL and GRB-2 in vivo is mediated by the binding of the GRB-2 SH2 domain to the phosphorylated tyrosine 177 in BCR-ABL. The GRB-2 SH3 domains apparently do not contribute to the in vivo binding between full length GRB-2 and BCR-ABL.

8. EXAMPLE
BCR-ABL Proteins Defective in GRB-2 Binding Exhibit Decreased Transforming Capacity The data presented in this Working Example demonstrates that the transformation potential of the BCR-ABL intracellular PTK is dependent upon the binding of this PTK to the GRB-2 member of the GRB subfamily of the adaptor family of proteins. This result represents the first case in which the binding of an adaptor protein to such a PTK is implicated as a step in a transformation/oncogenesis process.

8.1. Materials and Methods 8.1.1. Transformation Assays

Infection of Rat1 fibroblasts was carried out as previously described (Lugo et al., 1989, *Mol. Cell. Biol.* 9:1263–1270). Titers were in the range of >$10^5$ infectious particles per ml as determined by the frequency of gene transfer to fibroblasts. Rat1 colony formation in semisolid medium was measured by plating 5×$10^4$ cells per 6-cm$^2$ dish in 5 ml of Iscoves supplemented with 15% fetal calf serum and 0.4% Noble agar (Lugo et al., 1989, *Mol. Cell. Biol.* 9:1263–1270). G418-resistant populations were established by culturing the infected cells for 12–15 days in G518 (0.5 mg per ml). Following selection, cells from G418-resistant cultures were plated in agar at a density of 104 cells per ml. The number of colonies formed in the agar was recorded two weeks after plating the cells.

Infection and establishment of hematopoietic cell cultures from freshly isolated murine bone marrow were performed as previously described (McLaughlin et al., 1987, *Proc. Natl. Acad. Sci. USA* 84:6558–6562). In brief, bone marrow elements from 4–6 week old female BALB/c mice were resuspended at 2×$10^6$ cells per ml in the appropriate retroviral stock supplemented with 4 μg of Polybrene per ml. Cells were incubated for 4 hours at 37° C. Following infection, cells were washed and resuspended in RPMI 1640 medium supplemented with 5% fetal calf serum and 50 μM β-mercaptoethanol, at a density of $10^6$ cells per ml 5 ml of the cell suspension was plated into each 6 cm$^2$ dish. Cultures were maintained for up to 8 weeks and fresh media was added once a week. The cultures were considered transformed when the cell density of the nonadherent hematopoietic cells exceeded $10^6$ cells per ml.

8.1.2. Miscellaneous Procedures

Techniques in addition to the transformation assays as described in Section 8.1.1 are as those described, above, in Section 6.1.

8.2. Results

To determine the biological relevance of GRB-2 binding to BCR-ABL-induced oncogenesis, the effect of mutating tyrosine 177 was examined, required for association with GRB-2, on the ability of BCR-ABL to transform fibroblasts and hematopoietic cells. Helper-free retroviral stocks of wild type and mutant BCR-ABL forms were used to infect Rat1 fibroblasts and freshly isolated murine bone marrow cells. Both GRB-2 and hSos-I have been shown to be expressed in these cell types (Lowenstein et al., 1992, *Cell* 70:431–442; Bowtell et al., 1992, *Proc. Natl. Acad. Sci. USA* 89:6511–6515; Chardin et al., 1993, *Science* 260:1338–1343). Transformation of Rat1 fibroblasts was assayed by colony formation in soft agar (Lugo et al., 1989, *Mol. Cell. Biol.* 9:1263–1270). Hematopoietic cell transformation was assayed by culturing infected mouse bone marrow cells under conditions that support the growth of pre-B lymphocytes (McLaughlin et al., 1987, *Proc. Natl. Acad. Sci. USA* 84:6558–6562). In contrast to wild type BCR-ABL, the P185 (Y177F) protein did not transform hematopoietic cells and exhibited a decreased capacity to transform Rat1 cells (FIG. 10). These results are consistent with the previous observation that the P185 (Δ176–426) mutant which deletes Y177 exhibited decreased transforming activity in both Rat1 fibroblasts and hematopoietic cells (Muller et al., 1991, *Mol. Cell. Biol.* 11:1785–1792; FIG. 10). P185(Δ176–426) displays a more pronounced deficiency in the transformation of Rat1 fibroblasts than P185 (Y177F), particularly after G418 selection (FIG. 10). Sequences downstream of Y177 in the BCR first exon have been shown to bind to SH2 domains in a phosphoserine/phosphothreonine-dependent manner (Pendergast et al., 1991, *Cell* 66:161–171; Muller et al., 1991, *Mol. Cell. Biol.* 11:1785–1792). Two SH2-binding sites have been identified within this region (designated A and B) and removal of these sites may abolish specific protein interactions important for BCR-ABL-mediated transformation of fibroblasts. Both P185 (Y177F) and P185 (Δ176–426) showed no transformation activity in hematopoietic cells. Differences in the transforming activities of the BCR-ABL proteins were not due to different levels of protein expression. Western blot analysis of lysates from cells expressing the various BCR-ABL forms revealed comparable steady-state levels of the proteins following infection of Rat1 fibroblasts with the corresponding retroviruses (FIG. 11).

9. EXAMPLE
BCR-ABL Activities Transcription from a RAS-Responsive Element Promoter in a RAS-Dependent Manner In the Working Example presented in this section, it is demonstrated that BCR-ABL intracellular PTK/GRB-2 binding serves to activate the Ras signalling pathway.

9.1. Materials and Methods 9.1.1. Transcriptional Activation Assay

Transcriptional activation of expression from a Ras-responsive element (ets/AP-1) promoter was done essentially as described previously (Clark et al., 1993, *Proc. Natl. Acad. Sci. USA* 90:4887–4891; Hauser et al., 1993, *Methods*

*in Enzymology*, in press). Briefly, NIH 3T3 cells were transfected with 1 μg of the pB4X-CAT chloramphenicol acetyl transferase reporter plasmid (Wasylyk et al., 1989, *Mol. Cell. Biol.* 9:2247–2250), together with 0.5 μg pSRαMSVTkneo containing the indicated BCR-ABL mutants in the presence or absence of 5 μg pZIP H-Ras (17N) (Feig et al., 1988, *Mol. Cell. Biol.* 8:3235–3243). Transfections were performed in duplicate in 60 mm dishes and the cells harvested after 48 hr. Following lysis by freeze thaw in 100 μl of 250 mM Tris HCl (pH 7.8), cell debris was removed by centrifugation and the supernatant heated to 62° C. to denature endogenous acyl transferases. Following further centrifugation, a 50 μl aliquot of each supernatant was assayed for CAT activity by incubation with 0.1 μCi of $^{14}$C chloramphenicol (NEN) and 0.34 mM acetyl CoA i 250 mM Tris-HCl in a final reaction volume of 140 μl for 45 minutes. The reaction was then terminated by extraction with 500 μl of ethyl acetate, evaporated under vacuum, and the resulting pellets were redissolved and subjected to thin layer chromatography on silica gel plates, using 5% methanol/95% chloroform (v/v) as solvent. Assays were quantitated using an AMBIS beta scanner.

9.1.2. Miscellaneous Techniques

Techniques in addition to the transformation assays as described in Section 8.1.1 are as those described, above, in Section 6.1.

9.2. Results

A mechanism whereby GRB-2-binding to BCR-ABL may potentiate oncogenic transformation is through direct stimulation of Ras via the Sos-1 guanine nucleotide exchange factor. To examine whether the interaction of BCR-ABL with GRB-2 feeds directly into the Ras pathway a transcriptional activation assay has been employed. Oncogenic Ras increases the rate of transcription from Ras-responsive elements (e.g. ets-1 and AP-1 DNA motifs; Hauser et al., 1993, *Methods in Enzymology*, in press). In addition, oncogenes with a wide range of functions, including protein tyrosine kinases and serine/threonine kinases can activate transcription from promoters containing Ras-responsive elements such as the ets/AP-1 motif (Schweighoffer et al., 1992, *Science* 256:825–827). A correlation exists between the ability of various oncogenes to activate transcription from an ets/AP-1-containing promoter and their capacity to transform cells.(Wasylyk et al., 1988, *EMBO J.* 7:2475–2483). Thus, transactivation assays may complement the cell growth and tumorigenicity studies for the analysis of oncogene function.

Wild type and mutant forms of BCR-ABL were compared for their ability to activate transcription from ets/AP-1. A CAT reporter under the control of a β-globin promoter that contains four tandem Ras-responsive elements (pB4X-CAT). Oncogenic Ras has been shown to increase the rate of transcription from this element up to 15-fold (Schweighoffer, *Science* 256:825–827). As shown in FIG. 12, wild type BCR-ABL-induced activation is abolished by co-transfection of Ras (17N), a dominant inhibitory mutant which has been shown to neutralize Ras function (Feig et al., 1988, *Mol. Cell. Biol.* 8:3235–3243; Thomas et al., 1992, *Cell* 68:1031–1040; Wood et al., 1992, *Cell* 68:1041–1050) indicating that BCR-ABL-induced transcriptional activation is mediated by Ras. Significantly, the BCR-ABL mutants, P185 (Y177F) and P185 (Δ176–426), that are deficient for GRB-2 binding, produced little, if any, effect on transcriptional transactivation from this promoter (FIG. 11). The low level of transactivation obtained with the BCR-ABL mutants correlates with their decreased transforming activities compared to wild type P185 BCR-ABL (FIG. 10). Further, infection of Rat1 fibroblast cells with wild type BCR-ABL-containing retrovirus produces an increase in the fraction of Ras-GTP (FIG. 13). Quantitation of the amount of GDP and GTP bound to Ras with an AMBIS beta scanner shows a modest but reproducible increase.

10. EXAMPLE

Signaling Incompetent GRB2 Reverses the Phenotype of Transformed Cells

The following example shows that disruption of the signal transduction pathway involving BCR/ABL and GRB2 can reverse a transformed phenotype in cells. Elevated expression of signaling incompetent GRB2 mutants reverses BCR/ABL induced transformed growth in Rat 1 cells. Disruption of the signaling pathway also inhibits the growth of cells isolated from a patient with chronic myelogenous leukemia (K562 cells) that express BCR/ABL as well as transformed cells dependant on the PDGF receptor.

10.1. Materials and Methods

Mutant GRB2 genes were constructed that deleted the SH3 domain on either the amino (N') or carboxy (C') terminus. Full length and truncated forms of GRB2 were inserted into the Bam H1 site of a modified pCGN plasmid vector (Tanaka et al., *Cell* 60:375–386, 1990) as described in Pendergast et al., *Cell* 75:175–185, 1993. This vector has the hygromycin resistance gene inserted upstream of the SV40 origin of replication. To facilitate discrimination of the endogenous GRB2 protein from the transfected constructs, a sequence coding for the influenza virus hemagglutinin epitope (Pati, U. K., *Gene* 114:285–288, 1992) was fused in frame at the N terminus of the mutant proteins. The same antigenic tag was fused to the wild type GRB2 gene.

BCR/ABL transformed Rat 1 fibroblasts were established as described in Example 8.1.1 above. GRB2 constructs were transfected into Rat1-BCR/ABL cell lines and the rat glioman cell line C6 (ATCC CCL 107) using the standard calcium phosphate transfection protocol (Molecular Cloning Techniques, Laboratory Manual, 2nd Ed., Ed Sambrook et al., Cold-Spring Harbor Laboratory Press, 1989 and Muller). Following transfection, the Rat1 cells were cultured for 24 hrs, then exposed to the drugs G418+hygromycin (Sigma) for 7–9 days. The double drug selected mass population of cells were seeded in soft agar and the levels of endogenous BCR/ABL, GRB2 and transfected GRB2 determined using Western blot. Individual clonal cell lines expressing the different transfected GRB2 constructs were also established. In the case of transfected C6 cells, cells were selected in hygromycin containing media for 10 days as described in Muller, supra. Following drug selection, cells were seeded in soft agar medium containing 0.5% FCS and PDGF (1 ng/ml). Colonies >0.4 mm were counted on day 10.

Expression of the GRB2 constructs was evaluated by immunoprecipitation as described in Pendergast et al., *Cell* 75:175–185, 1993. Briefly, BCR/ABL-GRB2 expressing Rat1 cells were lysed and immunoprecipitated with anti-ABL pEx4 antibodies and the immunoprecipitates were subjected to an in vitro autokinase assay (Pendergast et al., supra). The samples were analyzed by SDS-PAGE gel and visualized by autoradiography. In a second experiment, cells were lysed in 10 mM Tris-HCl, ph 7.4, 1% SDS, 1 mM PMSF, 15 μg of protein from each sample was separated using SDS-PAGE (15%). The proteins were electrophoretically transferred to nitrocellulose filters and immunoblotted with an anti-GRB2 mouse monoclonal antibody (Transduction Laboratories) followed by incubation with goat anti mouse Mab conjugated to horse-radish peroxidase (BioRad). Proteins were visualized with the Enhanced Chemiluminescence detection system (Amersham).

Soft agar assays were performed as previously described (Lugo et al., Mol. Cell. Bio. 9:1263–1270, 1989). Mass populations of drug selected cells were seeded at densities ranging between $10^3$–$5\times10^4$ cells/6 cm$^2$ dish depending on the cloning efficiency of each cell type. Samples were plated in duplicate in medium containing 20% fetal calf serum. Macroscopic colonies (>0.4 mm) were counted after 14 days. The data represents the average number of colonies observed in 3 to 5 independent experiments performed with mass populations of transfected and drug selected cells. Data for the growth of Rat1-BCR/ABL was derived using three independent Rat1-BCR/ABL clonal cell lines transfected with the appropriate constructs and repeated in 2 to 3 separate experiments for each cell line. Thus the data represents the average number of colonies observed in 7 independent experiments.

K562 (ATCC CRL 243) cells were transfected with the GRB2 constructs using standard methods of electroporation. Following transfection, cells were cultured for 18 to 24 hrs, then exposed to hygromycin (500 μg/ml) for 2 days. After drug selection numbers of viable cells were determined by counting cells which exclude the dye trypan blue. Equal numbers of viable cells were seeded in soft agar.

10.2 Results 10.2.1. Expression of GRB2 in RAT 1 Cells

Expression of the N'GRB2 mutant protein in Rat1-BCR/ABL cells causes a reversion to a normal phenotype. The mass population of N' GRB2 mutant expressing cells grew as a monolayer in liquid culture and exhibited contact inhibition when reaching confluence. Significantly, N'GRB2 mutant expressing Rat1-BCR/ABL cells exhibited a dramatic reduction in their ability to form colonies in soft agar when compared to cells expressing the empty vector (see Table 1). Cells expressing the C'GRB2 mutant expressing cells grew as monolayers in liquid culture but did not quiesce when confluent. Growth of C'GRB2 mutant expressing Rat1-BCR/ABL fibroblasts in soft agar was also suppressed, albeit to a lesser extent than that observed for the N' GRB2 mutant. Because comparable ratios of mutant proteins to wild type GRB2 protein were present in both the N' and C' expressing cell population, the greater potency of the N' mutant to suppress BCR/ABL induced transformation is probably not simply due to differences in the level of the two mutants (FIG. 14B). Rather these differences may indicate that the two SH3 domains bind SOS with different affinities or bind to different substrates. Thus GRB2 SH3 deletion mutant proteins act as dominant negative inhibitors of BCR/ABL induced transformation when present in equimolar or greater amounts than the endogenous wild type GRB2 in the cell.

In contrast to the N' or C' GRB2 mutants, elevated expression of wild type GRB2 in Rat1-BCR/ABL fibroblasts appeared to accentuate the transformed phenotype. The drug selected mass population of cells expressing the transfected wild type GRB2 construct consistently exhibited a 25–30% increase in the number of colonies in soft agar when compared to cells transfected with the empty vector (Table 1). These data suggest that the GRB2 protein may be a limiting effector in BCR/ABL induced transformation of Rat 1 fibroblasts.

TABLE 1

| Construct | Rat1 | K562 | C6 |
| --- | --- | --- | --- |
| empty vector | 566 | 187 | 520 |
| wild type GRB2 | 734 | 209 | 577 |

TABLE 1-continued

| Construct | Rat1 | K562 | C6 |
| --- | --- | --- | --- |
| N' truncated GRB2 | 14 | 13 | 2 |
| C' truncated GRB2 | 119 | 86 | 3 |

(# Colonies/1 × $10^4$ cells seeded)

10.2.2. Expression of GRB2 Mutants in K562 Cells

The SH3 GRB2 mutants also inhibit the growth of human leukemic cells. The GRB2 constructs were introduced into K562 cells, a p210 BCR/ABL expressing cell line established from a CML patient in blast crisis. Following transfection and 48 hrs of drug selection, levels of endogenous BCR/ABL, GRB2 and transfected GRB2 were determined by Western blot (FIG. 16). At the same time, viable cells were seeded in soft agar. Cultures seeded with K562 cells expressing the N'GRB2 mutant protein showed 10 times fewer the number of soft agar colonies when compared to mock transfected controls (Table 1). Analogous to what was observed in the Rat1-BCR/ABL fibroblasts, the C'GRB2 mutant also inhibited K562 colony formation, but to a lesser degree than the N' mutant. These data indicate that signal transduction mediated by GRB2 is an essential component in BCR/ABL induced human malignancies.

10.2.3. Expression of GRB2 in C6 Gliona cells

The GRB2 constructs were also introduced into rat C6 glioma cells, which are dependant on PDGF receptor activity for their transformed growth phenotype (Zhang et al., Neurol. Res. 14(5):397–401, 1992). PDGF receptor has been shown to interact with GRB2 (Lowenstein et al., 1992, Cell 70:431–442). As shown in Table 1, expression of the signaling incompetent GRB2 mutants significantly inhibited colony formation. This data demonstrates that inhibition of GRB2 signal transduction is can be used to inhibit transformed cell growth that is dependant on receptor tyrosine kinase activation.

11. EXAMPLE

Signaling Incompetent GRB2 Prevents Tumor Growth in an Animal Model

This example demonstrates that cells expressing signaling incompetent GRB2 are no longer able to form tumors in animals, suggesting that disruption of the, BCR/ABL signaling pathway can be used to treat cancer in mammals.

11.1. Materials and Methods

GPB2 (wild type and mutants) and BCR/ABL expressing Rat 1 cells were prepared as described in Example 10. Nude mice (4 mice per group) were injected subcutaneously in the left flank with Rat 1 cells co-expressing p210 BCR/ABL and either wild type GRB2, N' truncated CRB2 or C' truncated GRB2. Cells expressing p210 BCR(ABL alone ($2\times10^6$ cells in 100 μl) were injected subcutaneously on the right hind leg of each mouse to act as an internal control. The mice were sacrificed at 3 weeks post-implant and the tumor volume measured.

11.2. Results

The results shown in Table 2 clearly demonstrate that expression of signaling incompetent GRB2 proteins reduces growth of tumor cells in vivo.

TABLE 2

| Group | left | right |
| --- | --- | --- |
| wild tpe GRB2 | 0.5 | 0.5 |
| N' truncated GRB2 | 0.3 | 0.7 |

TABLE 2-continued

| Group | left | right |
|---|---|---|
| C' truncated GRB2 | <0.1 | 0.7 |

(data shown is average tumor size per group)

12. EXAMPLE
Effects of Signaling Incompetent GRB2 on RAS Activation

This example shows that the signaling incompetent GRB2 molecules described herein inhibit BCR/ABL induced ras activation in proportion to their transformation inhibitory potency suggesting that interaction between GRB2 and downstream signaling components that lead to ras activation is disrupted.

12.1. Materials and Methods

Transcriptional activation of expression from a Ras-responsive element (ets/AP-1) promoter was done as described in Example 9. Transformation of Rat1 cells, soft agar assays and immunoblotting experiments were performed as described in Example 10.

12.2. Results

To determine whether the growth inhibitory effect of the GRB2 mutants was due to their ability to block ras activation, lysates prepared from Rat1-BCR/ABL cell lines hyperexpressing wild type or mutant GRB2 proteins were evaluated for their ability to activate ras. Using a ras dependent transcription activation assay, we observed that lysates from N' GRB2 expressing Rat1-BCR/ABL cells exhibited a 10–15 fold lower ras activation activity than mock transfected controls (FIG. 15). Lysates from C' GRB2 expressing cell lines also had a decrease in their ras activation activity, albeit to a lesser extent than that of the N' mutant. The difference in the inhibitory effect of the N' and C' mutants is consistent with their potency to reverse the BCR/ABL transformed phenotype.

If the GRB2 mutant proteins function by blocking intermediate steps in the signal transduction pathway prior to ras, then transformation by genes which circumvent ras activation should not be effected. To test this hypothesis, the GRB2 constructs were transfected into Rat 1 cells transformed with an activated form of raf, a serine kinase which elicits its mitogenic effect downstream of ras in the same signaling pathway (Kolch et al., Nature 349:426, 1991). Following drug selection with hygromycin the mass population of cells were seeded in agar. Rat1/v-raf cells expressing N' or C' GRB2 mutants gave rise to the same number of colonies in soft agar as the mock transfected control cells (Table 3). Furthermore, cell lines expressing a greater than two fold excess of SH3 mutant than endogenous wild type GRB2 protein were not inhibited in their ability to grow in soft agar (FIG. 16). These data suggest that the GRB2 mutant proteins inhibit the BCR/ABL mitogenic signal by uncoupling the signal transduction pathway upstream of raf.

TABLE 3

| Construct | Rat1/v-raf |
|---|---|
| empty vector | 620 |
| wild type GRB2 | 665 |
| N' truncated GRB2 | 653 |
| C' truncated GRB2 | 598 |

(# Colonies/1 × $10^4$ cells seeded)

It is apparent that many modifications and variations of this invention as set forth here may be made without departing from the spirit and scope thereof. The specific embodiments described hereinabove are given by way of example only and the invention is limited only by the terms of the appended claims.

What is claimed is:

1. A method for identifying a compound that disrupts a protein tyrosine phosphatase polypeptide/GRB-2 adaptor polypeptide complex comprising:

(a) contacting a cell that forms the complex with a compound that acts intracellularly at a concentration sufficient to disrupt the protein tyrosine phosphatase polypeptide/GRB-2 complex;

(b) detecting the level of the complex present in the cell of step (a); and (c) comparing the level of the complex detected in step (b) to the level of complex present in a cell of the type in step (a) that has not contacted the compound, so that if the level detected in step (b) is less than the level present in the cell, the compound that disrupts a protein tyrosine phosphatase polypeptide/GRB-2 adaptor polypeptide complex is identified.

2. The method of claim 1, wherein the GRB-2 adaptor polypeptide comprises a F-L-I-R-E-S (SEQ ID NO:4) or F-L-V-R-E-S (SEQ ID NO:5) amino acid sequence.

3. The method of claim 1, wherein the protein tyrosine phosphatase polypeptide comprises a X-P-X-Y-V/I-N-V/I (SEQ ID NO:6) amino acid sequence.

4. The method of claim 1, wherein said protein tyrosine phosphatase polypeptide is selected from the group consisting of CD45, LAR, RPTPα, RPTPβ, RPTPχ, and RPTPκ.

5. A method for identifying a compound to be tested for an ability to disrupt a protein tyrosine phosphatase polypeptide/GRB-2 adaptor polypeptide complex comprising: contacting a protein tyrosine phosphatase polypeptide or a GRB-2 adaptor polypeptide with a test compound for a time sufficient to allow binding of the test compound to the protein tyrosine phosphatase polypeptide or the GRB-2 adaptor polypeptide; so that if the test compound binds the protein tyrosine phosphatase polypeptide or the GRB-2 polypeptide, a compound to be tested for an ability to disrupt a protein tyrosine phosphatase/GRB-2 adaptor polypeptide complex is identified.

6. The method of claim 5, wherein the GRB-2 adaptor polypeptide comprises a F-L-I-R-E-S (SEQ ID NO:4) or F-L-V-R-E-S (SEQ ID NO:5) amino acid sequence.

7. The method of claim 5, wherein the protein tyrosine phosphatase polypeptide comprises X-P-X-Y-V/I-N-V/I (SEQ ID NO:6) amino acid sequence.

8. The method of claim 5, wherein said protein tyrosine phosphatase polypeptide is selected from the group consisting of CD45, LAR, RPTPα, RPTPβ, RPTPχ, and RPTPκ.

* * * * *

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 1

Asp Leu Arg Ala Ala Asn
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 2

Asp Leu Ala Ala Arg Asn
 1               5
```

```
<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: SITE
<222> LOCATION: (2)
<223> OTHER INFORMATION: Xaa=Ile or Val
<220> FEATURE:
<221> NAME/KEY: SITE
<222> LOCATION: (3)
<223> OTHER INFORMATION: Xaa=Lys or Arg
<220> FEATURE:
<221> NAME/KEY: SITE
<222> LOCATION: (5)
<223> OTHER INFORMATION: Xaa=Thr or Met

<400> SEQUENCE: 3

Pro Xaa Xaa Trp Xaa Ala Pro Glu
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 4

Phe Leu Ile Arg Glu Ser
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 5

Phe Leu Val Arg Glu Ser
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: SITE
<222> LOCATION: (1)
<223> OTHER INFORMATION: Xaa=any amino acid residue
<220> FEATURE:
<221> NAME/KEY: SITE
<222> LOCATION: (3)
<223> OTHER INFORMATION: Xaa=any amino acid residue
<220> FEATURE:
<221> NAME/KEY: SITE
<222> LOCATION: (5)
<223> OTHER INFORMATION: Xaa=Val or Ile
<220> FEATURE:
<221> NAME/KEY: SITE
<222> LOCATION: (7)
<223> OTHER INFORMATION: Xaa=Val or Ile

<400> SEQUENCE: 6
```

```
Xaa Pro Xaa Tyr Xaa Asn Xaa
  1               5
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: SITE
<222> LOCATION: (1)
<223> OTHER INFORMATION: Xaa=any amino acid residue
<220> FEATURE:
<221> NAME/KEY: SITE
<222> LOCATION: (3)
<223> OTHER INFORMATION: Xaa=any amino acid residue
<220> FEATURE:
<221> NAME/KEY: SITE
<222> LOCATION: (4)
<223> OTHER INFORMATION: Xaa=any amino acid residue
<220> FEATURE:
<221> NAME/KEY: SITE
<222> LOCATION: (8)
<223> OTHER INFORMATION: Xaa=a hydrophobic residue
<220> FEATURE:
<221> NAME/KEY: SITE
<222> LOCATION: (9)
<223> OTHER INFORMATION: Xaa=any amino acid residue

<400> SEQUENCE: 7

```
Xaa Pro Xaa Xaa Pro Pro Pro Xaa Xaa Pro
  1               5                  10
```

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: consensus
      sequence

<400> SEQUENCE: 8

```
Pro Pro Pro Val Pro Pro Arg Arg
  1               5
```

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: SITE
<222> LOCATION: (1)
<223> OTHER INFORMATION: Xaa=Ile or Val
<220> FEATURE:
<221> NAME/KEY: SITE
<222> LOCATION: (4)
<223> OTHER INFORMATION: Xaa=any amino acid residue
<220> FEATURE:
<221> NAME/KEY: SITE
<222> LOCATION: (7)
<223> OTHER INFORMATION: Xaa=any amino acid residue
<220> FEATURE:
<221> NAME/KEY: SITE
<222> LOCATION: (8)
<223> OTHER INFORMATION: Xaa=any amino acid residue
<220> FEATURE:
<221> NAME/KEY: SITE
<222> LOCATION: (10)

```
<223> OTHER INFORMATION: Xaa=Ser or Thr

<400> SEQUENCE: 9

Xaa His Cys Xaa Ala Gly Xaa Xaa Arg Xaa Gly
 1               5                  10

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
aagcccttct tcgttaacgt cgag                                           24

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: conserved
      motif

<400> SEQUENCE: 11

Val Ala Val Lys
 1

<210> SEQ ID NO 12
<211> LENGTH: 5
<212> TYPE: PRT
<213> ORGANISM: Artificial Sequence
<220> FEATURE:
<221> NAME/KEY: SITE
<222> LOCATION: (3)
<223> OTHER INFORMATION: Xaa=any amino acid residue
<220> FEATURE:
<223> OTHER INFORMATION: Description of Artificial Sequence: conserved
      motif

<400> SEQUENCE: 12

Gly Met Xaa Tyr Leu
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: conserved
      motif

<400> SEQUENCE: 13

Ile His Arg Asp Leu Ala Ala Arg Asn
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: conserved
      motif

<400> SEQUENCE: 14

Lys Trp Met Ala Pro Glu
 1               5
```

```
<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: conserved
      motif

<400> SEQUENCE: 15

Lys Trp Thr Ala Pro Glu
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: conserved
      motif

<400> SEQUENCE: 16

Phe Trp Tyr Ala Pro Glu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: conserved
      motif

<400> SEQUENCE: 17

Ser Asp Val Trp Ser Phe Gly
 1               5
```